US008114170B2

(12) United States Patent
Goget et al.

(10) Patent No.: US 8,114,170 B2
(45) Date of Patent: Feb. 14, 2012

(54) AGENT FOR COLORING AND/OR BLEACHING KERATIN FIBERS COMPRISING COMPOSITION (A), COMPOSITION (B), AT LEAST ONE FAT AND AT LEAST ONE REDUCTONE

(75) Inventors: Caroline Goget, Paris (FR); Gautier Deconinck, Saint-Gratien (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 12/976,150

(22) Filed: Dec. 22, 2010

(65) Prior Publication Data

US 2011/0146007 A1 Jun. 23, 2011

Related U.S. Application Data

(60) Provisional application No. 61/294,579, filed on Jan. 13, 2010.

(30) Foreign Application Priority Data

Dec. 22, 2009 (FR) ..................................... 09 59434

(51) Int. Cl.
*A61Q 5/10* (2006.01)
(52) U.S. Cl. ............. 8/405; 8/406; 8/410; 8/431; 8/435; 8/455; 8/602; 8/604
(58) Field of Classification Search ............. 8/405, 406, 8/410, 431, 435, 455, 602, 604
See application file for complete search history.

(56) References Cited

U.S. PATENT DOCUMENTS

| 3,100,739 | A | 8/1963 | Kaiser et al. |
| 3,369,970 | A | 2/1968 | McLaughlin et al. |
| 3,629,330 | A | 12/1971 | Brody et al. |
| 3,861,868 | A | 1/1975 | Milbrada |
| 4,138,478 | A | 2/1979 | Reese et al. |
| 4,170,637 | A | 10/1979 | Pum |
| 4,226,851 | A | 10/1980 | Sompayrac |
| 4,357,141 | A | 11/1982 | Grollier et al. |
| 4,366,099 | A | 12/1982 | Gaetani et al. |
| 4,488,564 | A | 12/1984 | Grollier et al. |
| 4,725,282 | A | 2/1988 | Hoch et al. |
| 4,826,681 | A | 5/1989 | Jacquet et al. |
| 4,845,293 | A | 7/1989 | Junino et al. |
| 5,021,066 | A | 6/1991 | Aeby et al. |
| 5,259,849 | A | 11/1993 | Grollier et al. |
| 5,364,414 | A | 11/1994 | Lang et al. |
| 5,817,155 | A | 10/1998 | Yasuda et al. |
| 6,010,541 | A | 1/2000 | De la Mettrie |
| 6,074,439 | A | 6/2000 | De La Mettrie et al. |
| 6,129,770 | A | 10/2000 | Deutz et al. |
| 6,156,713 | A | 12/2000 | Chopra et al. |
| 6,165,444 | A | 12/2000 | Dubief et al. |
| 6,190,421 | B1 | 2/2001 | Rondeau et al. |
| 6,206,935 | B1 | 3/2001 | Onitsuka et al. |
| 6,238,653 | B1 | 5/2001 | Narasimhan et al. |
| 6,251,378 | B1 | 6/2001 | Laurent et al. |
| 6,260,556 | B1 | 7/2001 | Legrand et al. |
| 6,277,154 | B1 | 8/2001 | Lorenz |
| 6,277,155 | B1 | 8/2001 | De La Mettrie et al. |
| 6,365,136 | B1 | 4/2002 | Lauscher et al. |
| 6,423,100 | B1 | 7/2002 | Lang et al. |
| 6,447,552 | B1 | 9/2002 | Golinski |
| 6,645,258 | B2 | 11/2003 | Vidal et al. |
| 6,660,045 | B1 | 12/2003 | Hoeffkes et al. |
| 6,695,887 | B2 | 2/2004 | Cottard et al. |
| 6,800,098 | B1 | 10/2004 | Allard et al. |
| 7,135,046 | B2 | 11/2006 | Audousset |
| 7,153,331 | B2 | 12/2006 | Desenne et al. |
| 7,217,298 | B2 | 5/2007 | Legrand et al. |
| 7,285,137 | B2 | 10/2007 | Vidal et al. |
| 7,442,215 | B2 | 10/2008 | Audousset et al. |
| 7,458,993 | B2 | 12/2008 | Cottard et al. |
| 7,494,513 | B2 | 2/2009 | Kravtchenko et al. |
| 7,575,605 | B2 | 8/2009 | Legrand |
| 7,651,533 | B2 | 1/2010 | Legrand |
| 7,651,536 | B2 | 1/2010 | Cottard et al. |

(Continued)

FOREIGN PATENT DOCUMENTS

CA    1 268 421    5/1990

(Continued)

OTHER PUBLICATIONS

STIC Search Report dated May 13, 2011.*
French Search Report for FR 0959434, dated Sep. 24, 2010.
English language abstract of FR 2 925 308 A1, Jun. 26, 2009.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.

(Continued)

*Primary Examiner* — Eisa Elhilo
(74) *Attorney, Agent, or Firm* — Finnegan, Henderson, Farabow, Garrett & Dunner, LLP

(57) ABSTRACT

The present disclosure relates to an agent for coloring and/or bleaching keratin fibers, consisting of: a first composition (A) comprising at least one alkalizing agent, and a second composition (B) comprising at least one oxidizing agent, wherein at least one of the two compositions (A) and (B) comprises at least one fat selected from liquid hydrocarbons, such that the at least one fat is present in a mixture of compositions (A) and (B) in an amount of at least 20 wt. %, relative to the total weight of the mixture, and further wherein at least one of compositions (A) and (B) comprises at least one reductone optionally in a form chosen from acids, salts, and esters. The present disclosure also relates to a method of coloring and/or bleaching keratin fibers employing the agent, as well as a kit containing it.

30 Claims, No Drawings

U.S. PATENT DOCUMENTS

| | | |
|---|---|---|
| 7,740,663 B2 | 6/2010 | De La Mettrie et al. |
| 7,766,977 B2 | 8/2010 | Cottard et al. |
| 7,799,095 B2 | 9/2010 | Mario et al. |
| 2003/0064494 A1 | 4/2003 | Kumar et al. |
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0221400 A1 | 11/2004 | Cotteret et al. |
| 2004/0226110 A1 | 11/2004 | LeGrand |
| 2004/0235700 A1 | 11/2004 | Legrand et al. |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1* | 11/2006 | Legrand .......................... 8/405 |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |
| 2010/0162492 A1 | 7/2010 | Hercouet et al. |
| 2010/0175705 A1 | 7/2010 | Hercouet et al. |
| 2010/0186177 A1 | 7/2010 | Hercouet et al. |
| 2010/0199441 A1 | 8/2010 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 A2 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 047 841 A1 | 4/2009 |
| EP | 2 072 034 A1 | 6/2009 |
| EP | 2 072 035 | 6/2009 |
| EP | 2 072 036 | 6/2009 |
| EP | 2 198 842 A2 | 6/2010 |
| EP | 2 198 843 A1 | 6/2010 |
| EP | 2 198 849 A1 | 6/2010 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 A1 | 6/2009 |
| FR | 2 925 309 | 6/2009 |
| FR | 2 925 311 | 6/2009 |
| FR | 2 940 054 A1 | 6/2010 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |

| | | |
|---|---|---|
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
Copending U.S. Appl. No. 12/976,093, filed Dec. 22, 2010.
Copending U.S. Appl. No. 12/976,124, filed Dec. 22, 2010.
Copending U.S. Appl. No. 12/976,173, filed Dec. 22, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of Jp 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.

French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
French Search Report for FR 09/59388, dated Aug. 3, 2010.
French Search Report for FR 09/59391, dated Sep. 16, 2010.
French Search Report for FR 09/59433, dated Sep. 24, 2010.
International Search Report for PCT/FR2009/052617, dated Mar. 30, 2010.
LookChem, poly[(dimethyliminio)-1,1,6-hexanediylchloride (1:2)], pp. 1-2, accesses Mar. 7, 2011.
Notice of Allowance mailed Apr. 1, 2011, in U.S. Appl. No. 12/642,506.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed in co-pending U.S. Appl. No. 12/339,753, dated Jul. 9, 2010.
Notice of Allowance mailed Jan. 28, 2011, in U.S. Appl. No. 12/642,592.
Notice of Allowance mailed Jun. 11, 2010, in U.S. Appl. No. 12/642,489.
Notice of Allowance mailed Mar. 9, 2011, in U.S. Appl. No. 12/642,473.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Dec. 17, 2010, in co-pending U.S. Appl. No. 12/642,451.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Mar. 16, 2011, in co-pending U.S. Appl. No. 12/642,583.
Office Action mailed Mar. 29, 2011, in co-pending U.S. Appl. No. 12/642,468.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

AGENT FOR COLORING AND/OR BLEACHING KERATIN FIBERS COMPRISING COMPOSITION (A), COMPOSITION (B), AT LEAST ONE FAT AND AT LEAST ONE REDUCTONE

This application claims benefit of U.S. Provisional Application No. 61/294,579, filed Jan. 13, 2010. This application also claims benefit of priority under 35 U.S.C. §119 to French Patent Application No. 0959434, filed Dec. 22, 2009.

The present disclosure relates to an agent in two parts for coloring and/or bleaching keratin fibers, for example human keratin fibers such as the hair.

The present disclosure thus relates to an agent for coloring and/or bleaching keratin fibers, consisting of a first composition (A) comprising at least one alkalizing agent and optionally at least one oxidation dye and/or at least one direct dye, and a second composition (B) comprising at least one oxidizing agent, wherein at least one of the compositions (A) and (B) comprises at least one fat, and at least one reductone.

The present disclosure also relates to a multi-compartment device, containing the coloring and/or bleaching agent disclosed herein.

The present disclosure similarly relates to a method of coloring and/or bleaching keratin fibers, employing the agent disclosed herein.

For a long time, people have tried to alter the color of their hair, such as by bleaching it, or conversely by coloring it, for example in order to mask white hair.

For coloring human keratin fibers, generally two types of dyeing have been developed.

The first type of dyeing is so-called "permanent" or "oxidation dyeing," which employs dyeing compositions containing oxidation dye precursors, generally called oxidation bases. These oxidation bases may be colorless or slightly colored compounds which, together with oxidizing products, can give rise to colored compounds by a process of oxidative condensation.

It is also known that the shades obtained with these oxidation bases may be varied by combining them with dyeing couplers or modifiers. The variety of molecules used as oxidation bases and couplers can provide a rich palette of colors.

The second type of dyeing is called "semi-permanent" or "direct dyeing," which consists of applying, on the keratin fibers, direct dyes which are colored and coloring molecules having an affinity for said fibers, waiting, and then rinsing.

The direct dyes generally used for said dyeing may be selected from benzene, anthraquinone, nitropyridine, azo, xanthene, acridine, azine, and triarylmethane nitro direct dyes.

A method of this type does not require the use of an oxidizing agent for developing the coloration. However, it is possible to use such an agent, in order to obtain an effect of lightening with coloration. This is then called "direct" or "semi-permanent dyeing in lightening conditions."

The methods of permanent or semi-permanent dyeing in lightening conditions may therefore require using, with the dyeing composition, an aqueous composition comprising at least one oxidizing agent, in many cases at alkaline pH.

The typical methods for bleaching human keratin fibers entail using an aqueous composition comprising at least one oxidizing agent, generally at alkaline pH. The role of this oxidizing agent is to degrade the melanin in the hair, which, depending on the nature of the oxidizing agent present, may lead to a more or less pronounced lightening of the fibers. Thus, for relatively slight lightening, the oxidizing agent is generally hydrogen peroxide. When a greater degree of lightening is required, usually peroxidized salts are employed, for example persulphates, in the presence of hydrogen peroxide.

One of the difficulties that may be encountered during application of these known methods of coloring and bleaching arise from the fact that they are employed in alkaline conditions.

To improve the performance of the methods for coloring and/or bleaching human keratin fibers, and to limit the disadvantages connected with the use of alkaline agents and oxidizing agents, it has been proposed to use a substantial amount of at least one fat in the dyeing compositions.

However, during preparation of a fat-enriched mixture of a composition comprising an alkaline agent and a composition comprising an oxidizing agent, intense coloration of the mixture may develop, which may be unattractive, and moreover may reflect undesirable degradation of certain compounds.

The applicants have discovered that certain antioxidants in the reductone class, in the presence of at least one fat selected from the liquid hydrocarbons, may reduce the undesirable coloration of the mixture.

The present disclosure therefore relates to an agent for coloring and/or bleaching keratin fibers, consisting of:
a first composition (A) comprising at least one alkalizing agent, and
a second composition (B) comprising at least one oxidizing agent,
wherein at least one of the compositions (A) and (B) comprises at least one fat selected from liquid hydrocarbons, such that the at least one fat is present in a mixture of compositions (A) and (B) in an amount of at least 20 wt. %, relative to the total weight of the mixture, and
further wherein at least one of compositions (A) and (B) comprises at least one reductone optionally in a form chosen from acids, salts, and esters.

When the agent according to the disclosure is used for coloring, optionally with lightening, keratin fibers, composition (A) may further comprise at least one oxidation dye and/or at least one direct dye.

Conversely, when the agent according to the disclosure is used only for bleaching keratin fibers, neither composition (A) nor composition (B) comprise at least one direct dye and/or at least one oxidation dye (bases and couplers). or, if at least one direct dye and/or at least one oxidation dye happen to be present, the at least one direct dye and/or at least one oxidation dye may be present in a total amount of less than 0.005 wt. % relative to the total weight of the respective composition. At such an amount, only the composition would be colored, i.e. no effect of coloring of the keratin fibers would be observed.

The coloring and/or bleaching agent according to the present disclosure does not become colored during mixing of the two compositions (A) and (B) or during subsequent application of the compositions on keratin fibers, or if a coloring effect does occur, it remains very moderate.

Moreover, when it is intended for coloring keratin fibers, the agent disclosed herein may be effective with respect to the strength of coloration obtained, as well as with respect to chromaticity, and the selectivity of coloration of one and the same fiber or the selectivity of coloration between fibers that are differently sensitized.

When it is intended for bleaching keratin fibers, the agent disclosed herein can offer performance in lightening that is equivalent or even greater than that obtained with existing compositions, for example with those based on ammonium hydroxide.

The agent disclosed herein may also have the feature that it limits pungent odors during its preparation, or its application on the fibers.

Other characteristics and features of the present disclosure herein will become clearer on reading the description and examples given below.

In what follows, and unless stated otherwise, the limits of a range of values are included in this range.

The human keratin fibers treated by the method disclosed herein are for example hair.

According to the present disclosure, composition (A) comprises at least one alkalizing agent.

The alkalizing agent can for example be a mineral or organic base.

For instance, the alkalizing agent may be selected from ammonia, alkaline carbonates, sodium hydroxide, potassium hydroxide, organic amines such as for example alkanolamines and the derivatives thereof, and compounds of formula (I):

$$\begin{array}{c} R_x \\ \diagdown \\ \phantom{X}N-W-N \\ \diagup \phantom{XXXX} \diagdown \\ R_y \phantom{XXXXXX} R_t \end{array} \quad (I)$$

wherein W is chosen from $C_1$-$C_6$ alkylene residues optionally substituted with a hydroxyl group or a $C_1$-$C_6$ alkyl radical; and Rx, Ry, Rz, and Rt, which may be identical or different, are chosen from a hydrogen atom, $C_1$-$C_6$ alkyls, $C_1$-$C_6$ hydroxyalkyls, and $C_1$-$C_6$ aminoalkyl radicals.

As examples of compounds of formula (I), non-limiting mention may, for example, be made of 1,3-diaminopropane, 1,3-diamino-2-propanol, spermine, and spermidine.

The alkalizing agents that may for example be used are the alkanolamines, such as the mono-, di- and triethanolamines.

In at least one embodiment of the agent disclosed herein, the alkalizing agent is monoethanolamine.

According to another embodiment, composition (A) comprises, as the at least one alkalizing agent, at least one organic amine, such as for example at least one alkanolamine. When composition (A) comprises several alkalizing agents including an alkanolamine and ammonia or the salts thereof, the amount by weight of the at least one organic amine present in composition (A) may be greater than the amount by weight of ammonia present in composition (A).

According to at least one embodiment of the present disclosure, composition (A) does not comprise ammonia.

According to at least one embodiment, when composition (A) contains ammonia or the salts thereof, it also contains at least one alkanolamine, and the amount by weight of the at least one alkanolamine present in composition (A) may be greater than the amount by weight of ammonia present in the composition.

Generally, composition (A) comprises at least one alkalizing agent present in an amount ranging from 0.1 to 40 wt. %, such as from 0.5 to 20 wt. %, relative to the weight of the composition.

In at least one embodiment, composition (A) has a pH greater than or equal to 8, such as a pH ranging from 8.5 to 11.5.

This pH can also be adjusted to the desired value by using, for example, as well as the alkalizing agent, at least one acidifying agent.

Among the acidifying agents, non-limiting mention may be made, as examples, of mineral or organic acids such as hydrochloric acid, orthophosphoric acid, sulphuric acid; carboxylic acids such as acetic acid, tartaric acid, citric acid, lactic acid; and sulphonic acids.

According to the present disclosure, composition (B) comprises at least one oxidizing agent.

The at least one oxidizing agent can be selected from the oxidizing agents typically used for bleaching and oxidation dyeing of keratin fibers, and among which non-limiting mention may be made of hydrogen peroxide, urea peroxide, bromates or ferricyanides of alkali metals, peroxidized salts for example persulphates, perborates and percarbonates of alkali metals or alkaline-earth metals such as sodium, potassium, magnesium. It is also possible to use, as oxidizing agent, at least one redox enzyme such as laccases, peroxidases, and 2-electron oxidoreductases (such as uricase), optionally in the presence of the respective donor or cofactor thereof.

In at least one embodiment, hydrogen peroxide may for example be used. It can be used for example in aqueous solution (hydrogen peroxide solution), in an amount ranging, for instance, from 0.1 to 50 wt. %, such as from 0.5 to 20 wt. %, for example from 1 to 15 wt. %, relative to the total weight of composition (B).

Depending on the degree of bleaching desired, the at least one oxidizing agent can also comprise at least one compound for example selected from the peroxidized salts.

In at least one embodiment of the agent according to the present disclosure, the pH of composition (B) is below 7. The pH can be adjusted to the desired value by using at least one acidifying agent, which can for example be selected from those described above.

According to the present disclosure, at least one of compositions (A) and (B) comprises at least one reductone optionally in a form chosen from acids, salts, and esters. Thus, the at least one reductone can be present in composition (A), composition (B), or compositions (A) and (B) at the same time.

In at least one embodiment, the at least one reductone is present in composition (A) and/or composition (B) in an amount ranging from 0.01 to 1 wt. %, for example from 0.05 to 0.5 wt. %, such as from 0.1 to 0.25 wt. %, relative to the total weight of the respective composition (A) and/or composition (B).

According to at least one embodiment, composition (A) comprises at least one reductone. For example, the at least one reductone may be only present in composition (A).

In at least one embodiment, the at least one reductone in the mixture of compositions (A) and (B) is present in an amount ranging from 0.01 to 1 wt. %, for example from 0.05 to 0.5 wt. %, such as from 0.1 to 0.2 wt. %, relative to the total weight of the mixture.

According to the present disclosure, the percentages by weight of the at least one reductone may be expressed relative to the acid form of the at least one reductone.

As is known in the art, the term "reductone" denotes a compound comprising an enediol structure —(HO)C=C(OH)— adjacent to a carbonyl group >C=O.

Thus, the at least one reductone usable in the present disclosure may be chosen from those of general formula (II):

$$R_1-(HO)C=C(OH)-\underset{\underset{O}{\|}}{C}-R_2 \quad (II)$$

wherein $R_1$ and $R_2$, which may be identical or different, each denote a group containing at least one carbon atom and/or oxygen atom, and $R_1$ and $R_2$ can form, with the three carbon atoms of the compound of formula (II), a ring, for instance with 5 or 6 ring members, whose additional constituent atoms are constituted of carbon atoms and/or oxygen atoms.

In at least one embodiment, $R_1$ and $R_2$ form, with the three carbon atoms of the at least one compound of formula (II), a ring with 5 carbon atoms and/or oxygen atoms.

The at least one compound of formula (II) can for example be in a form chosen from acids, salts, and esters. As non-limiting examples of the at least one reductone in salt form, non-limiting mention may be made of salts of alkali metals such as sodium and potassium salts, and salts of alkaline-earth metals such as calcium and magnesium salts. As non-limiting examples of the at least one reductone in ester form, non-limiting mention may be made of esters of $C_8$ to $C_{30}$ fatty acids.

In at least one embodiment disclosed herein, the at least one compound of formula (II) is a lactone.

The at least one reductone can for example be selected from reductic acid, ascorbic acid, erythorbic or isoascorbic acid, and the salts thereof, such as the sodium or potassium salts, ascorbyl palmitate, and mixtures thereof.

For example, the at least one reductone may be selected from ascorbic acid, erythorbic acid, and the salts of thereof, such as the sodium or potassium salts thereof.

As mentioned above, at least one of compositions (A) and (B) comprises at least one fat selected from the liquid hydrocarbons, such that the at least one fat is present in a mixture of compositions (A) and (B) in an amount of at least 20 wt. %, relative to the total weight of the mixture.

Thus, the at least one fat can be present in composition (A), in composition (B), or in compositions (A) and (B) at the same time, provided that the total amount of the at least one fat in the mixture of compositions (A) and (B) is at least equal to 20 wt. %, relative to the total weight of the mixture of the compositions.

In at least one embodiment disclosed herein, the total amount of the at least one liquid hydrocarbon in the mixture of compositions (A) and (B) is at least 25 wt. %, such as at least 30 wt. %, relative to the total weight of the mixture.

The total amount of the at least one liquid hydrocarbon in the mixture of compositions (A) and (B) may for example be less than or equal to 90 wt. %, such as less than or equal to 70 wt. %, relative to the total weight of the mixture.

According to at least one embodiment disclosed herein, composition (A) comprises at least one fat selected from the liquid hydrocarbons.

"Fat" means, in the present disclosure, an organic compound that is insoluble in water at normal temperature (25° C.) and at atmospheric pressure (760 mmHg), i.e. which has a solubility in water below 5 wt. % and for example below 1 wt. %, such as below 0.1 wt. %. The structure of the at least one fat has at least one sequence of at least two siloxane groups or a hydrocarbon chain having at least 6 carbon atoms. Moreover, the at least one fat is generally soluble in organic solvents in the same conditions as temperature and pressure, for example chloroform, ethanol, benzene, liquid paraffin, and decamethylcyclopentasiloxane.

According to the present disclosure, the at least one fat is selected from the liquid hydrocarbons.

"Liquid hydrocarbon" means a hydrocarbon composed solely of carbon atoms and hydrogen atoms, which is liquid at normal temperature (25° C.) and at atmospheric pressure (760 mmHg; or $1.013 \times 10^5$ Pa).

For example, the liquid hydrocarbons according to the present disclosure may be selected from:

linear or branched, optionally cyclic, $C_6$-$C_{16}$ lower alkanes. As non-limiting examples, mention may be made of hexane, undecane, dodecane, tridecane; and isoparaffins such as isohexadecane, isododecane, and isodecane.

linear or branched hydrocarbons, of mineral, animal or synthetic origin, containing more than 16 carbon atoms, such as paraffin oils, liquid paraffin, polydecenes, hydrogenated polyisobutenes such as Parleam®, and squalane.

In at least one embodiment of the disclosure, the at least one liquid hydrocarbon is selected from paraffin oils, liquid paraffin, and mixtures thereof.

Composition (A) and/or composition (B) according to the present disclosure can also comprise at least one additional fat, different from the aforementioned liquid hydrocarbons, which does not contain a carboxylic acid function.

"Fat not containing a carboxylic acid function" means a fat that does not contain a —COOH group or a —COO⁻ group.

The at least one additional fat can for example be selected from non-silicone oils of vegetable or synthetic origin, other than the liquid hydrocarbons disclosed herein, fatty alcohols, esters of fatty acid and/or of fatty alcohol, non-silicone waxes, and silicones.

It is to be recalled that, for purposes of the present disclosure, the alcohols, esters, and fatty acids may have at least one hydrocarbon group, linear or branched, saturated or unsaturated, comprising 6 to 30 carbon atoms, optionally substituted, for example with at least one hydroxyl group (for example from 1 to 4). If they are unsaturated, these compounds can comprise one to three, conjugated or unconjugated, carbon-carbon double bonds.

As oils of vegetable or synthetic origin usable in the agent disclosed herein, non-limiting mention may for example be made of:

triglyceride oils of vegetable or synthetic origin, such as the liquid triglycerides of fatty acids having from 6 to 30 carbon atoms, such as the triglycerides of heptanoic or octanoic acids or, for example, sunflower oil, maize oil, soya oil, cucurbit oil, grapeseed oil, sesame oil, hazelnut oil, apricot oil, macadamia oil, arara oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, and karite butter oil.

fluorinated oils such as perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; and derivatives of perfluoromorpholine, such as 4-trifluoromethyl perfluoromorpholine sold under the name PF 5052® by the company 3M.

It is also possible to use petroleum jelly.

The fatty alcohols suitable for the agent disclosed herein may for example be selected from saturated or unsaturated, linear or branched alcohols having from 8 to 30 carbon atoms. Non-limiting mention may for example be made of cetyl alcohol, stearyl alcohol and their mixture (cetylstearyl alcohol), octyldodecanol, 2-butyloctanol, 2-hexyldecanol, 2-undecylpentadecanol, oleic alcohol, and linoleic alcohol.

Regarding the esters of fatty acid and/or of fatty alcohol, for example different from the triglycerides mentioned above, non-limiting mention may for example be made of the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, non-limiting mention may for example be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, myristyl, stearyl myristate, hexyl stearate, butyl stearate, isobutyl stearate; dioctyl maleate, hexyl laurate, and 2-hexyldecyl laurate.

In at least one embodiment disclosed herein, it is also possible to use esters of $C_4$-$C_{22}$ di- or tricarboxylic acids and of $C_1$-$C_{22}$ alcohols and esters of mono-, di- or tricarboxylic acids and of $C_2$-$C_{26}$ di-, tri-, tetra- or pentahydroxy alcohols.

Non-limiting mention may also be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisotearyl citrate; glyceryl trilactate; glyceryl trioctanoate; trioctyldodecyl citrate; trioleyl citrate, propylene glycol dioctanoate; neopentyl glycol diheptanoate; diethylene glycol diisanonate; and polyethylene glycol distearates.

Among the esters mentioned above, the following may for example be used: ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl maleate, hexyl laurate, 2-hexyldecyl laurate and isononyl isononanoate, and cetyl octanoate.

The agent according to the present disclosure can also comprise, as fatty ester, esters and di-esters of sugars of $C_6$-$C_{30}$, such as $C_{12}$-$C_{22}$ fatty acids. It should be mentioned that "sugar" means oxygenated hydrocarbon compounds possessing several alcohol functions, with or without an aldehyde or ketone function, and which have at least 4 carbon atoms. These sugars can be monosaccharides, oligosaccharides, or polysaccharides.

As suitable sugars, non-limiting mention may for example be made of sucrose, glucose, galactose, ribose, fucose, maltose, fructose, mannose, arabinose, xylose, lactose, and their derivatives, for instance alkylated, such as methylated, derivatives, such as methylglucose.

The esters of sugars and of fatty acids can be selected for example from the group comprising the esters or mixtures of esters of sugars described above and of $C_6$-$C_{30}$, such as $C_{12}$-$C_{22}$, linear or branched, saturated or unsaturated fatty acids. If they are unsaturated, these compounds can comprise one to three, conjugated or unconjugated, carbon-carbon double bonds.

The esters according to this embodiment can also be selected from mono-, di-, tri- and tetra-esters, polyesters and mixtures thereof.

These esters can be for example oleates, laurates, palmitates, myristates, behenates, cocoates, stearates, linoleates, linolenates, caprates, arachidonates, or mixtures thereof such as for example oleo-palmitate, oleo-stearate, and palmito-stearate mixed esters.

For instance, mono- and di-esters are used, such as mono- or di-oleate, stearate, behenate, oleopalmitate, linoleate, linolenate, and oleostearate, of sucrose, of glucose, or of methylglucose.

Non-limiting mention may for example be made of the product sold under the name GLUCATE® DO by the company Amerchol, which is a methylglucose dioleate.

Non-limiting mention may also be made as examples of esters or of mixtures of esters of sugar of fatty acid:

the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and sucrose mono-laurate;

the products sold under the name RYOTO SUGAR ESTERS, for example referenced B370, and corresponding to sucrose behenate formed from 20% of monoester and 80% of di-triester-polyester;

the sucrose mono-di-palmito-stearate marketed by the company Goldschmidt under the name TEGOSOFT® PSE.

The wax or waxes (non-silicone) may for example be selected from carnauba wax, candelilla wax, and alfa wax, paraffin wax, ozokerite, vegetable waxes such as olive wax, rice wax, hydrogenated jojoba wax or absolute waxes of flowers such as essential wax of blackcurrant flower sold by the company BERTIN (France), animal waxes such as beeswaxes, or modified beeswaxes (Cera Bellina); other waxes or waxy raw materials usable according to the present disclosure are for example marine waxes such as that sold by the company SOPHIM under reference M82, and waxes of polyethylene or of polyolefins in general.

The silicones usable in the agent according to the present disclosure are volatile or non-volatile, cyclic, linear or branched silicones, unmodified or modified with organic groups, having a viscosity from $5 \times 10^{-6}$ to 2.5 m$^2$/s at 25° C., such as from $1 \times 10^{-5}$ to 1 m$^2$/s.

The silicones usable according to the present disclosure can be in the form of oils, waxes, resins, or gums.

For example, the silicone may be selected from the polydialkylsiloxanes, such as the polydimethylsiloxanes (PDMS), and the organo-modified polysiloxanes having at least one functional group selected from the poly(oxyalkylene) groups, amino groups, and alkoxy groups.

The organopolysiloxanes are defined in more detail in the work of Walter NOLL "Chemistry and Technology of Silicones" (1968), Academic Press. They can be volatile or non-volatile.

When they are volatile, the silicones may for example be selected from those having a boiling point ranging from 60° C. to 260° C., and for instance from:

cyclic polydialkylsiloxanes having 3 to 7, such as from 4 to 5 silicon atoms. These are, for example, octamethylcyclotetrasiloxane marketed under the name VOLATILE SILICONE® 7207 by UNION CARBIDE or SILBIONE® 70045 V2 by RHODIA, decamethylcyclopentasiloxane marketed under the name VOLATILE SILICONE® 7158 by UNION CARBIDE, and SILBIONE® 70045 V5 by RHODIA, and mixtures thereof.

Non-limiting mention may also be made of the cyclocopolymers of the dimethylsiloxanes/methylalkylsiloxane type, such as SILICONE VOLATILE® FZ 3109 marketed by the company UNION CARBIDE, of formula:

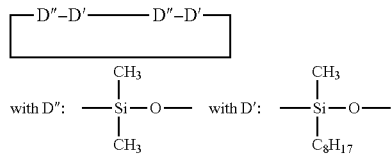

Non-limiting mention may also be made of the mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy) bis-neopentane; the volatile linear polydialkylsiloxanes having 2 to 9 silicon atoms and with a viscosity less than or equal to $5 \times 10^{-6}$ m$^2$/s at 25° C. An example is decamethyltetrasiloxane marketed for example under the name SH 200 by the company TORAY SILICONE. Silicones included in this class are also described in the article published in Cosmetics and Toiletries, Vol. 91, Jan. 76, P. 27-32—TODD & BYERS "Volatile Silicone fluids for cosmetics."

Non-volatile polydialkylsiloxanes, gums, and resins of polydialkylsiloxanes, polyorganosiloxanes modified with the aforementioned organofunctional groups, and mixtures thereof, may for example be used.

These silicones may for instance be chosen from the polydialkylsiloxanes, among which non-limiting mention may be made of the polydimethylsiloxanes with trimethylsilyl end groups. The viscosity of the silicones is measured at 25° C. according to standard ASTM 445 Appendix C.

Among these polydialkylsiloxanes, non-limiting mention may, for example, be made of the following commercial products:

the SILBIONE® oils of series 47 and 70 047 or the MIRASIL® oils marketed by RHODIA such as, for example, the oil 70 047 V 500 000;

the oils of the MIRASIL® series marketed by the company RHODIA;

the oils of the 200 series from the company DOW CORNING such as DC200 with a viscosity of 60,000 mm$^2$/s; and the VISCASIL® oils from GENERAL ELECTRIC and certain oils of the SF series (SF 96, SF 18) from GENERAL ELECTRIC.

Non-limiting mention may for example be made of the polydimethylsiloxanes with dimethylsilanol end groups known under the name dimethiconol (CTFA), such as the oils of the 48 series from the company RHODIA.

In this class of polydialkylsiloxanes, non-limiting mention may also be made of the products marketed under the names ABIL WAX® 9800 and 9801 by the company GOLDSCHMIDT, which are polydialkyl ($C_1$-$C_{20}$) siloxanes.

The silicone gums usable according to the present disclosure are for example polydialkylsiloxanes, such as polydimethylsiloxanes having high number-average molecular weights ranging from 200,000 to 1,000,000 used alone or mixed in a solvent. The solvent can be selected from volatile silicones, polydimethylsiloxane oils (PDMS), polyphenylmethylsiloxane oils (PPMS), isoparaffins, polyisobutylenes, methylene chloride, pentane, dodecane, tridecane, and mixtures thereof.

Products usable for example according to the present disclosure are mixtures such as:

mixtures formed from a chain end hydroxylated polydimethylsiloxane, or dimethiconol (CTFA) and a cyclic polydimethylsiloxane also called cyclomethicone (CTFA) such as the product Q2 1401 marketed by the company DOW CORNING;

mixtures of a polydimethylsiloxane gum and of a cyclic silicone such as the product SF 1214 Silicone Fluid from the company GENERAL ELECTRIC. The product is a gum SF 30 corresponding to a dimethicone, having a number-average molecular weight of 500,000 dissolved in oil SF 1202 Silicone Fluid corresponding to decamethylcyclopentasiloxane;

mixtures of two PDMS of different viscosities, and for example of a PDMS gum and a PDMS oil, such as the product SF 1236 from the company GENERAL ELECTRIC. The product SF 1236 is a mixture of a gum SE 30, as defined above, having a viscosity of 20 m$^2$/s, and of an oil SF 96 with a viscosity of $5 \times 10^{-6}$ m$^2$/s. This product may comprise 15% of SE 30 gum and 85% of SF 96 oil.

The resins of organopolysiloxanes usable according to the present disclosure are crosslinked siloxane systems containing the units:

$R_2SiO_{2/2}$, $R_3SiO_{1/2}$, $RSiO_{3/2}$ and $SiO_{4/2}$ wherein R represents an alkyl having 1 to 16 carbon atoms. Among these resins, non-limiting mention may for example be made of those wherein R denotes a $C_1$-$C_4$ lower alkyl group, such as methyl.

Non-limiting mention may for example be made, among these resins, of the product marketed under the name "DOW CORNING 593" or those marketed under the names "SILICONE FLUID SS 4230 and SS 4267" by the company GENERAL ELECTRIC, which are silicones of dimethyl/trimethyl siloxane structure.

Non-limiting mention may also be made of the resins of the trimethylsiloxysilicate type for instance marketed under the names X22-4914, X21-5034, and X21-5037 by the company SHIN-ETSU.

The organomodified silicones usable according to the present disclosure may be silicones as defined previously and have in their structure at least one organofunctional group fixed via a hydrocarbon group.

Apart from the silicones described above, the organomodified silicones can also be polydiaryl siloxanes, such as polydiphenylsiloxanes, and polyalkyl-arylsiloxanes functionalized with the organofunctional groups mentioned previously.

The polyalkarylsiloxanes are selected for example from linear and/or branched polydimethyl/methylphenylsiloxanes, and polydimethyl/diphenylsiloxanes with a viscosity in the range from $1 \times 10^{-5}$ to $5 \times 10^{-2}$ m$^2$/s at 25° C.

Among these polyalkarylsiloxanes non-limiting mention may for example be made of the products marketed under the following names:

the SILBIONE® oils of the 70 641 series from RHODIA;

the oils of the RHODORSIL® series 70 633 and 763 from RHODIA;

the oil DOW CORNING 556 COSMETIC GRAD FLUID from DOW CORNING;

the silicones of the PK series from BAYER such as the product PK20;

the silicones of the PN, PH series from BAYER such as products PN1000 and PH1000;

certain oils of the SF series from GENERAL ELECTRIC such as SF 1023, SF 1154, SF 1250, SF 1265.

Among the organomodified silicones, non-limiting mention may for example be made of the polyorganosiloxanes comprising:

polyethyleneoxy and/or polypropyleneoxy groups optionally comprising $C_6$-$C_{24}$ alkyl groups such as the products called dimethicone copolyol marketed by the company DOW CORNING under the name DC 1248, the oils SILWET® L 722, L 7500, L 77, L 711 from the company UNION CARBIDE, and the alkyl ($C_{12}$)-methicone copolyol marketed by the company DOW CORNING under the name Q2 5200;

substituted or unsubstituted amino groups such as the products marketed under the name GP 4 Silicone Fluid and GP 7100 by the company GENESEE, and the products marketed under the names Q2 8220 and DOW CORNING 929 or 939 by the company DOW CORNING. The substituted amino groups may for example be $C_1$-$C_4$ aminoalkyl groups;

alkoxylated groups, such as the product marketed under the name SILICONE COPOLYMER F-755 by SWS SILICONES and ABIL WAX® 2428, 2434, and 2440 by the company GOLDSCHMIDT.

In at least one embodiment, the at least one additional fat is liquid at a temperature of 25° C. and at atmospheric pressure.

The at least one additional fat may for example be selected from fatty alcohols, esters of fatty acid, esters of fatty alcohol, vegetable or synthetic non-silicone oils different from the liquid hydrocarbons of the agent disclosed herein, silicones, and mixtures thereof.

For example, the at least one additional fat may be selected from the liquid esters of fatty acids and/or of fatty alcohols, the liquid fatty alcohols, and mixtures thereof.

The total amount of the at least one additional fat present in the mixture of compositions (A) and (B) can range from 0.1 to 40 wt. %, for instance from 0.5 to 25 wt. %, such as from 1 to 20 wt. %, relative to the total weight of the mixture.

According to at least one embodiment, composition (A) comprises at least one additional fat as described herein, in an amount for example ranging from 1 to 20 wt. %, relative to the total weight of composition (A).

Compositions (A) and/or (B) according to the present disclosure can further comprise at least one surfactant.

In this case, the at least one surfactant may for example be selected from the non-ionic surfactants and the anionic surfactants.

The at least one anionic surfactant may for example be selected from the salts (for instance salts of alkali metals, such as sodium salts; ammonium salts; salts of amines such as salts of amino alcohols; and salts of alkaline-earth metals such as magnesium salts) of the following compounds:

alkylsulphates, alkylethersulphates, alkylamidoethersulphates, alkarylpolyethersulphates, monoglyceride sulphates;

alkylsulphonates, alkylamidesulphonates, alkarylsulphonates, α-olefin-sulphonates, paraffin-sulphonates;

alkylphosphates, alkyletherphosphates;

alkylsulphosuccinates, alkylethersulphosuccinates, alkylamide-sulphosuccinates; alkylsulphosuccinamates;

alkylsulphoacetates;

acylsarcosinates; acylisethionates and N-acyltaurates;

salts of fatty acids such as oleic, ricinoleic, palmitic, stearic acids, acids of copra oil or of hydrogenated copra oil;

salts of alkyl D galactoside uronic acids;

acyl-lactylates;

salts of polyoxyalkylated alkyl ether carboxylic acids, polyoxyalkylated alkaryl ether carboxylic acids, polyoxyalkylated alkylamidoether carboxylic acids, such as those having from 2 to 50 ethylene oxide groups; and mixtures thereof.

It is to be noted that the alkyl or acyl radical of these various compounds may for example have from 6 to 24 carbon atoms, such as from 8 to 24 carbon atoms, with the aryl radical for instance denoting a phenyl or benzyl group.

The at least one non-ionic surfactant may for example be selected from the mono- or poly-oxyalkylated, and mono- or poly-glycerolated non-ionic surfactants. The oxyalkylated units may for example be ethoxylated, oxypropylated units, or a combination thereof, such as ethoxylated.

As examples of oxyalkylated non-ionic surfactants, non-limiting mention may be made of:

oxyalkylated alkyl($C_8$-$C_{24}$)phenols, saturated or unsaturated, linear or branched, oxyalkylated, $C_8$-$C_{30}$ alcohols, saturated or unsaturated, linear or branched, oxyalkylated, $C_8$-$C_{30}$ amides, esters of saturated or unsaturated, linear or branched, $C_8$-$C_{30}$ acids, and of polyethylene glycols, esters of saturated or unsaturated, linear or branched, $C_8$-$C_{30}$ acids, and of polyethoxylated sorbitol, saturated or unsaturated, ethoxylated vegetable oils, condensates of ethylene oxide and/or of propylene oxide, among others, and mixtures thereof.

These surfactants have a number of moles of ethylene oxide and/or of propylene oxide ranging from 1 to 100, such as from 2 to 50. In at least one embodiment, the at least one non-ionic surfactant does not comprise oxypropylated units.

According to at least one embodiment of the present disclosure, the at least one oxyalkylated non-ionic surfactant may be selected from ethoxylated $C_8$-$C_{30}$ alcohols, and the esters of $C_8$-$C_{30}$ acids, saturated or unsaturated, linear or branched, and of polyethoxylated sorbitol.

As examples of mono- or poly-glycerolated non-ionic surfactants, mono- or poly-glycerolated $C_8$-$C_{40}$ alcohols may for example be used.

For example, the mono- or poly-glycerolated $C_8$-$C_{40}$ alcohols may be chosen from those of formula:

RO—[$CH_2$—CH($CH_2$OH)—O]$_m$—H wherein R represents a linear or branched, $C_8$-$C_{40}$ radical, for instance a $C_8$-$C_{30}$ alkyl or alkenyl radical, and m represents a number ranging in value from 1 to 30, such as from 1 to 10.

As examples of compounds that may be suitable within the scope of the present disclosure, non-limiting mention may for example be made of lauric alcohol with 4 moles of glycerol (INCI name: POLYGLYCERYL-4 LAURYL ETHER), lauric alcohol with 1.5 moles of glycerol, oleic alcohol with 4 moles of glycerol (INCI name: POLYGLYCERYL-4 OLEYL ETHER), oleic alcohol with 2 moles of glycerol (INCI name: POLYGLYCERYL-2 OLEYL ETHER), cetearyl alcohol with 2 moles of glycerol, cetearyl alcohol with 6 moles of glycerol, oleocetyl alcohol with 6 moles of glycerol, and octadecanol with 6 moles of glycerol.

The alcohol can represent a mixture of alcohols, just as the value of m represents a statistical value, which signifies that, in a commercial product, several species of polyglycerolated fatty alcohols can coexist in the form of a mixture.

Among the mono- or poly-glycerolated alcohols, $C_8$/$C_{10}$ alcohol with one mole of glycerol, $C_{10}$/$C_{12}$ alcohol with 1 mole of glycerol, and $C_{12}$ alcohol with 1.5 mole of glycerol may for example be used.

According to the present disclosure, at least one non-ionic surfactant is preferred.

According to at least one embodiment, composition (A) comprises at least one surfactant.

The at least one surfactant can be present in composition (A) and/or (B) in an amount ranging from 0.1 to 50 wt. %, such as from 0.5 to 30 wt. %, relative to the total weight of each of composition (A) and/or (B) in which the at least one surfactant is contained.

Compositions (A) and/or (B) according to the present disclosure can also comprise at least one mineral thickener selected from organophilic clays, pyrogenic silicas, and mixtures thereof.

The at least one organophilic clay can be selected from montmorillonite, bentonite, hectorite, attapulgite, sepiolite, and mixtures thereof. The clay may be for example a bentonite or a hectorite.

These clays can be modified with a chemical compound selected from quaternary amines, tertiary amines, amino acetates, imidazolines, aminated soaps, fatty sulphates, alkaryl sulphonates, amine oxides, and mixtures thereof.

As organophilic clays, non-limiting mention may for example be made of the quaternium-18 bentonites such as those sold under the names BENTONE 3, BENTONE 38, and BENTONE 38V by the company Rheox, TIXOGEL VP by the company United Catalyst, and CLAYTONE 34, CLAYTONE 40, and CLAYTONE XL by the company Southern Clay; the stearalkonium bentonites such as those sold under the names BENTONE 27 by the company Rheox, TIXOGEL LG by the company United Catalyst, and CLAYTONE AF and CLAYTONE APA by the company Southern Clay; the quaternium-18/benzalkonium bentonites such as those sold under the names CLAYTONE HT and CLAYTONE PS by the company Southern Clay.

The pyrogenic silicas can be obtained by high-temperature hydrolysis of a volatile silicon compound in an oxyhydrogen flame, producing a finely divided silica. This process may for example give hydrophilic silicas that have a large number of silanol groups on their surface. Hydrophilic silicas of this kind are marketed for example under the names AEROSIL 130®, AEROSIL 200®, AEROSIL 255®, AEROSIL 300®, and AEROSIL 380® by the company Degussa, CAB-O-SIL HS-5®, CAB-O-SIL EH-5®, CAB-O-SIL LM-130®, CAB-O-SIL MS-55®, and CAB-O-SIL M-5® by the company Cabot.

It is possible for the surface of the silica to be modified chemically by chemical reaction to reduce the number of silanol groups. For example, silanol groups can be replaced with hydrophobic groups: a hydrophobic silica is then obtained.

The hydrophobic groups can be:

trimethylsiloxyl groups, which may for example be obtained by treatment of pyrogenic silica in the presence of hexamethyldisilazane. Silicas thus treated are called "Silica silylate" according to the CTFA (6th edition, 1995). They are for example marketed under the references AEROSIL R812® by the company Degussa and CAB-O-SIL TS-530® by the company Cabot.

dimethylsilyloxyl or polydimethylsiloxane groups, which may for example be obtained by treatment of pyrogenic silica in the presence of polydimethylsiloxane or dimethyldichlorosilane. Silicas thus treated are called "Silica dimethyl silylate" according to the CTFA (6th edition, 1995). They are for example marketed under the references AEROSIL R972® and AEROSIL R974® by the company Degussa, and CAB-O-SIL TS-610® and CAB-O-SIL TS-720® by the company Cabot.

The pyrogenic silica may for example have a particle size from nanometric to micrometric, for example ranging from 5 to 200 nm.

In at least one embodiment, the at least one mineral thickener is selected from hectorites, organomodified bentonites, and pyrogenic silicas, optionally modified.

When present, the at least one mineral thickener is present in an amount ranging from 1 to 30 wt. % relative to the weight of the composition in which it is present.

Compositions (A) and/or (B) according to the present disclosure can also comprise at least one organic thickener.

The at least one organic thickener can be selected for example from the amides of fatty acids (diethanol- or monoethanolamide of copra, monoethanolamide of ethoxylated alkyl ether carboxylic acid), polymeric thickeners such as cellulosic thickeners (hydroxyethylcellulose, hydroxypropylcellulose, carboxymethylcellulose), guar gum and its derivatives (hydroxypropylguar), gums of microbial origin (xanthan gum, scleroglucan gum), crosslinked homopolymers of acrylic acid or of acrylamidopropanesulphonic acid and associative polymers (polymers comprising hydrophilic zones, and hydrophobic zones with a fatty chain (alkyl, alkenyl comprising at least 10 carbon atoms) capable, in an aqueous medium, of associating reversibly with one another or with other molecules.

According to at least one embodiment, the at least one organic thickener is selected from cellulosic thickeners (hydroxyethylcellulose, hydroxypropylcellulose, carboxymethylcellulose), guar gum and its derivatives (hydroxypropylguar), gums of microbial origin (xanthan gum, scleroglucan gum), and crosslinked homopolymers of acrylic acid or of acrylamidopropanesulphonic acid, and for example from cellulosic thickeners such as hydroxyethylcellulose.

The at least one organic thickener, when present, is present in a total amount ranging from 0.01% to 20 wt. %, such as from 0.1 to 5 wt. %, relative to the weight of each composition in which it is present.

In at least one embodiment of the agent disclosed herein, composition (A) is in the form of a gel or a cream.

In at least one embodiment of the agent disclosed herein, composition (B) is in the form of a solution, an emulsion, or a gel.

According to at least one embodiment of the present disclosure, composition (A) further comprises at least one oxidation dye.

In such a case, the agent according to the present disclosure may for example be used for the oxidation dyeing of keratin fibers.

In this embodiment, composition (A) can further comprise at least one direct dye.

According to another embodiment of the present disclosure, composition (A) further comprises at least one direct dye.

In such a case, and when composition (A) does not comprise oxidation dyes, the agent according to the present disclosure may for example be used for direct dyeing of keratin fibers with lightening.

The at least one oxidation dye usable in the agents disclosed herein are in general selected from oxidation bases, and optionally combined with at least one coupler.

The at least one oxidation base may for example be selected from paraphenylenediamines, bis-phenylalkylenediamines, para-aminophenols, ortho-aminophenols, heterocyclic bases, and the addition salts thereof.

Among the paraphenylenediamines, non-limiting mention may be made for example of paraphenylenediamine, para-toluoylenediamine, 2-chloro-para-phenylenediamine, 2,3-dimethyl paraphenylenediamine, 2,6-dimethyl paraphenylenediamine, 2,6-diethyl paraphenylenediamine, 2,5-dimethyl paraphenylenediamine, N,N-dimethyl paraphenylenediamine, N,N-diethyl paraphenylenediamine, N,N-dipropyl paraphenylenediamine, 4-amino-N,N-diethyl-3-methyl aniline, N,N-bis(β-hydroxyethyl) paraphenylenediamine, 4-N,N-bis(β-hydroxyethyl)amino-2-methyl aniline, 4-N,N-bis(β-hydroxyethyl)amino-2-chloroaniline, 2-β-hydroxyethyl paraphenylenediamine, 2-fluoro-paraphenylenediamine, 2-isopropyl paraphenylenediamine, N-(β-hydroxypropyl) paraphenylenediamine, 2-hydroxymethyl paraphenylenediamine, N,N-dimethyl-3-methyl paraphenylenediamine, N,N-(ethyl, β-hydroxyethyl) paraphenylenediamine, N-(β,γ-dihydroxypropyl) paraphenylenediamine, N-(4'-aminophenyl) paraphenylenediamine, N-phenyl paraphenylenediamine, 2-β-hydroxyethyloxy paraphenylenediamine, 2-β-acetylaminoethyloxy paraphenylenediamine, N-(β-methoxyethyl) paraphenylenediamine, 4-aminophenylpyrrolidine, 2-thienyl paraphenylenediamine, 2-βhydroxyethylamino-5-aminotoluene, 3-hydroxy-1-(4'-aminophenyl)pyrrolidine, and the addition salts thereof with an acid.

Among the paraphenylenediamines mentioned above, paraphenylenediamine, paratoluoylenediamine, 2-isopropyl paraphenylenediamine, 2-β-hydroxyethyl paraphenylenediamine, 2-β-hydroxyethyloxy paraphenylenediamine, 2,6-dimethyl paraphenylenediamine, 2,6-diethyl paraphenylenediamine, 2,3-dimethyl paraphenylenediamine, N,N-bis-(β-hydroxyethyl) paraphenylenediamine, 2-chloro-paraphenylenediamine, 2-β-acetylaminoethyloxy paraphenylenediamine, and the addition salts thereof with an acid may for example be used.

Among the bis-phenylalkylenediamines, non-limiting mention may be made for example of N,N'-bis(β-hydroxyethyl) N,N'-bis(4'-aminophenyl)-1,3-diaminopropanol, N,N'-bisβ-hydroxyethyl) N,N'-bis(4'-aminophenyl)ethylenediamine, N,N'-bis(4-aminophenyl) tetramethylenediamine, N,N'-bis(β-hydroxyethyl) N,N'-bis(4-aminophenyl) tetramethylenediamine, N,N'-bis(4-methyl-aminophenyl) tetramethylenediamine, N,N'-bis(ethyl) N,N'-bis(4'-amino, 3'-methylphenyl)ethylenediamine, 1,8-bis(2,5-diaminophenoxy)-3,6-dioxaoctane, and the addition salts thereof.

Among the para-aminophenols, non-limiting mention may be made for example of para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl aminomethyl)phenol, 4-amino-2-fluorophenol, and the addition salts thereof with an acid.

Among the ortho-aminophenols, non-limiting mention may be made for example of 2-aminophenol, 2-amino-5-methylphenol, 2-amino-6-methylphenol, 5-acetamido-2-aminophenol, and the addition salts thereof.

Among the heterocyclic bases, non-limiting mention may be made for example of pyridine derivatives, pyrimidine derivatives, and pyrazole derivatives.

Among the pyridine derivatives, non-limiting mention may be made of the compounds described for example in patents GB 1 026 978 and GB 1 153 196, such as 2,5-diaminopyridine, 2-(4-methoxyphenyl)amino-3-aminopyridine, 3,4-diaminopyridine, and the addition salts thereof.

Other pyridine oxidation bases that may be useful in the present disclosure, as non-limiting examples, are the oxidation bases 3-aminopyrazolo-[1,5-a]-pyridines or the addition salts thereof described for example in patent application FR 2801308. As examples, non-limiting mention may be made of pyrazolo[1,5-a]pyridin-3-ylamine; 2-acetylaminopyrazolo-[1,5-a]pyridin-3-ylamine; 2-morpholin-4-yl-pyrazolo[1,5-a]pyridin-3-ylamine; 3-amino-pyrazolo[1,5-a]pyridine-2-carboxylic acid; 2-methoxy-pyrazolo[1,5-a]pyridin-3-ylamino; (3-amino-pyrazolo[1,5-a]pyridin-7-yl)-methanol; 2-(3-amino-pyrazolo[1,5-a]pyridin-5-yl)-ethanol; 2-(3-amino-pyrazolo[1,5-a]pyridin-7-yl)-ethanol; (3-amino-pyrazolo[1,5-a]pyridin-2-yl)-methanol; 3,6-diamino-pyrazolo[1,5-a]pyridine; 3,4-diamino-pyrazolo[1,5-a]pyridine; pyrazolo[1,5-a]pyridine-3,7-diamine; 7-morpholin-4-yl-pyrazolo[1,5-a]pyridin-3-ylamine; pyrazolo[1,5-a]pyridine-3,5-diamine; 5-morpholin-4-yl-pyrazolo[1,5-a]pyridin-3-ylamine; 2-[(3-amino-pyrazolo[1,5-a]pyridin-5-yl)-(2-hydroxyethyl)-amino]-ethanol; 2-[(3-amino-pyrazolo[1,5-a]pyridin-7-yl)-(2-hydroxyethyl)-amino]-ethanol; 3-amino-pyrazolo[1,5-a]pyridin-5-ol; 3-amino-pyrazolo[1,5-a]pyridin-4-ol; 3-amino-pyrazolo[1,5-a]pyridin-6-ol; and 3-amino-pyrazolo[1,5-a]pyridin-7-ol; as well as the addition salts thereof.

Among the pyrimidine derivatives, non-limiting mention may be made of the compounds described for example in publication nos. DE 2359399; JP 2-19576; JP 05-63124; EP 0770375, or WO 96/15765 such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the addition salts thereof and the tautomeric forms thereof, when there is tautomeric equilibrium.

Among the pyrazole derivatives, non-limiting mention may be made of the compounds described in patents DE 3843892, DE 4133957 and patent application publications WO 94/08969, WO 94/08970, FR-A-2 733 749 and DE 195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl pyrazole, 4,5-diamino-3-methyl-1-phenyl pyrazole, 4,5-diamino-1-methyl-3-phenyl pyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl) 3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethyl pyrazole, 4,5-diamino-3-hydroxymethyl-1-methylpyrazole, 4,5-diamino-3-hydroxymethyl-1-isopropyl pyrazole, 4,5-diamino-3-methyl-1-isopropyl pyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. It is also possible to use 4-5-diamino-1-(β-methoxyethyl)pyrazole.

In at least one embodiment, a 4,5-diaminopyrazole may be used, such as 4,5-diamino-1-(β-hydroxyethyl)-pyrazole and/or a salt thereof.

As pyrazole derivatives, non-limiting mention may be made for example of the diamino-N,N-dihydropyrazolopyrazolones and for instance those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a] pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydro-pyrazol-3-one, 4,5-diamino-1,2-diethyl-1,2-dihydro-pyrazol-3-one, 4,5-diamino-1,2-di-(2-hydroxyethyl)-1,2-dihydro-pyrazol-3-one, 2-amino-3-(2-hydroxyethyl)amino-6,7-dihydro-1H,5H-pyrazolo[1,2-a] pyrazol-1-one, 2-amino-3-dimethylamino-6,7-dihydro-1H, 5H-pyrazolo[1,2-a]pyrazol-1-one, 2,3-diamino-5,6,7,8- tetrahydro-1H,6H-pyridazino[1,2-a]pyrazol-1-one, 4-amino-1,2-diethyl-5-(pyrrolidin-1-yl)-1,2-dihydro-pyrazol-3-one, 4-amino-5-(3-dimethylamino-pyrrolidin-1-yl)-1,2-diethyl-1,2-dihydro-pyrazol-3-one, and 2,3-diamino-6-hydroxy-6,7-dihydro-1H,5H-pyrazolo[1,2-a]pyrazol-1-one.

In at least one embodiment, 2,3-diamino-6,7-dihydro-1H, 5H-pyrazolo[1,2-a]pyrazol-1-one and/or one of its salts may for example be used.

As heterocyclic bases, 4,5-diamino-1-(β-hydroxyethyl) pyrazole and/or 2,3-diamino-6,7-dihydro-1H,5H-pyrazolo[1,2-a]pyrazol-1-one and/or a salt thereof may for example be used.

As non-limiting examples, the at least one coupler usable in the present disclosure can be selected from those conventionally used for dyeing keratin fibers.

Among these couplers, non-limiting mention may be made for example of meta-phenylenediamines, meta-aminophenols, meta-diphenols, naphthalenic couplers, and heterocyclic couplers, as well as the addition salts thereof.

As examples, non-limiting mention may for example be made of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino) 1-methoxybenzene, 1,3-diaminobenzene, 1,3-bis(2, 4-diaminophenoxy)propane, 3-ureido aniline, 3-ureido-1-dimethylaminobenzene, sesamol, 1-β-hydroxyethylamino-3, 4-methylenedioxybenzene, α-naphthol, 2-methyl-1-naphthol, 6-hydroxyindole, 4-hydroxyindole, 4-hydroxy-N-methyl indole, 2-amino-3-hydroxypyridine, 6-hydroxybenzomorpholine-3,5-diamino-2,6-dimethoxypyridine, 1-N-(β-hydroxyethyl)amino-3,4-methylene dioxybenzene, 2,6-bis(β-hydroxyethylamino)toluene, 6-hydroxy indoline, 2,6-dihydroxy-4-methylpyridine, 1-H-3-methylpyrazol-5-one, 1-phenyl 3-methylpyrazol-5-one, 2,6-dimethylpyrazolo[1,5-b]-1,2,4-triazole, 2,6-dimethyl[3,2-c]-1,2, 4-triazole, 6-methyl pyrazolo[1,5-a]-benzimidazole, the addition salts thereof with an acid, and mixtures thereof.

Generally, the addition salts thereof of the at least one oxidation base and of the at least one coupler usable within the scope of the present disclosure may for example be selected from addition salts with an acid, such as hydrochlorides, hydrobromides, sulphates, citrates, succinates, tartrates, lactates, tosylates, benzenesulphonates, phosphates, and acetates.

The at least one oxidation base can each be present in an amount for example ranging from 0.0001 to 10 wt. % relative to the total weight of composition (A), such as from 0.005 to 5 wt. % relative to the total weight of the composition.

The at least one coupler, if present, can be present in an amount ranging for example from 0.0001 to 10 wt. % relative to the total weight of composition (A), such as from 0.005 to 5 wt. % relative to the total weight of the composition.

The at least one direct dye that can be used in composition (A) may for example be selected from ionic and non-ionic species, such as cationic and non-ionic.

As examples of at least one direct dye that may be suitable, non-limiting mention may for example be made of azo; methine; carbonyl; azine; (hetero)aryl nitro; tri-(hetero)aryl methane direct dyes; the porphyrins; the phthalocyanines, and natural direct dyes, alone or mixed.

For instance, the azo dyes may comprise a function —N═N— in which the two nitrogen atoms are not simultaneously inserted in a ring. It is not excluded, however, that one of the two nitrogen atoms of the —N═N— chain may be inserted in a ring.

The dyes of the methine class may for example be compounds comprising at least one sequence selected from >C═C< and —N═C< wherein the two atoms are not simultaneously inserted in a ring. It is specified, however, that one of the nitrogen or carbon atoms of the sequences can be inserted in a ring. In at least one embodiment, the dyes of this class may be derived from compounds such as methine, azomethine, mono- and diarylmethane, indoamines (or diphenylamines), indophenols, indoanilines, carbocyanines, azacarbocyanines and their isomers, diazacarbocyanines and their isomers, tetraazacarbocyanines, and hemicyanines.

Regarding the dyes of the carbonyl class, non-limiting mention may be made for example of the dyes selected from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso) violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, and coumarin.

Regarding the dyes of the cyclic azine class, non-limiting mention may for example be made of azine, xanthene, thioxanthene, fluorindine, acridine, (di)oxazine, (di)thiazine, and pyronine.

The (hetero)aromatic nitro dyes may for example be benzene-type or pyridine-type nitro direct dyes.

Regarding the porphyrin or phthalocyanine dyes, it is possible to use cationic or non-cationic compounds, optionally comprising at least one metal or metal ion, for example alkali metals and alkaline-earth metals, zinc, and silicon.

As examples of the at least one direct dye that may be used, non-limiting mention may be made of nitro dyes of the benzene series; the azo; azomethine; methine direct dyes; the azacarbocyanines such as tetraazacarbocyanines (tetraazapentamethines); the quinone direct dyes such as anthraquinone, naphthoquinone or benzoquinone direct dyes; the azine; xanthene; triarylmethane; indoamine; indigoid direct dyes; the phthalocyanines, porphyrins and natural direct dyes, alone or mixed.

These dyes can be monochromophoric dyes (i.e. only comprising a single dye) or polychromophoric dyes, for example di- or tri-chromophoric; and the chromophores can be identical or different, of the same or different chemical classes. Note that a polychromophoric dye comprises several radicals each derived from a molecule that absorbs in the visible region between 400 and 800 nm. Moreover, this absorbance of the dye does not require its prior oxidation, nor combination with other chemical species.

In the case of polychromophoric dyes, the chromophores are joined together by at least one linkage, which can be cationic or non-cationic.

In at least one embodiment, the linkage is a linear, branched or cyclic $C_1$-$C_{20}$ alkyl chain, optionally interrupted by at least one heteroatom (such as nitrogen, oxygen) and/or by at least one group containing one (CO, $SO_2$), optionally interrupted by at least one heterocycle, condensed or not, with a phenyl nucleus and comprising at least one quaternized nitrogen atom inserted in said ring and optionally at least one other heteroatom (such as oxygen, nitrogen or sulphur), optionally interrupted by at least one phenyl or naphthyl group, substituted or unsubstituted, optionally at least one quaternary ammonium group substituted with two $C_1$-$C_{15}$ alkyl groups, optionally substituted; the linkage not comprising a nitro, nitroso or peroxo group.

If the heterocycles or aromatic rings are substituted, they may for example be substituted with at least one $C_1$-$C_8$ alkyl radical optionally substituted with a hydroxyl group, $C_1$-$C_2$ alkoxy, $C_2$-$C_4$ hydroxyalkoxy, acetylamino, amino substituted with one or two $C_1$-$C_4$ alkyl radicals, optionally bearing at least one hydroxyl group, or the two radicals can form, with the nitrogen atom to which they are attached, a heterocycle with 5 or 6 ring members, optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two $C_1$-$C_4$ alkyl radicals, which may be identical or different, optionally bearing at least one hydroxyl group.

Among the benzene direct dyes usable according to the present disclosure, mention may be made, as a non-exhaustive list, of the following compounds:

1,4-diamino-2-nitrobenzene,
1-amino-2-nitro-4-β-hydroxyethylaminobenzene,
1-amino-2-nitro-4-bis(β-hydroxyethyl)-aminobenzene,
1,4-bis(β-hydroxyethylamino)-2-nitrobenzene,
1-β-hydroxyethylamino-2-nitro-4-bis(β-hydroxyethylamino)-benzene,
1-β-hydroxyethylamino-2-nitro-4-aminobenzene,
1-β-hydroxyethylamino-2-nitro-4-(ethyl)(β-hydroxyethyl)-aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-tris(hydroxymethyl)-methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis(β-hydroxyethyl)-amino-3-nitrobenzene,
1-β-hydroxyethylamino-2-nitrobenzene, and
1-hydroxy-4-β-hydroxyethylamino-3-nitrobenzene.

Among the azo, azomethine, methine or tetraazapentamethine direct dyes usable according to the present disclosure, non-limiting mention may be made of the cationic dyes described in patent application publications WO 95/15144, WO 95/01772, EP 714954, FR 2189006, FR 2285851, FR-2140205, EP 1378544, and EP 1674073.

Thus, non-limiting mention may for example be made of the following dyes of formulae (I) to (IV) given below, and for instance the compounds of the following formulae (I) and (III):

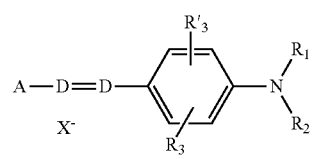
(I)

wherein:
D represents a nitrogen atom or —CH group,
$R_1$ and $R_2$, which may be identical or different, are chosen from a hydrogen atom; a $C_1$-$C_4$ alkyl radical which can be substituted with a —CN, —OH or —NH$_2$ radical or can form with a carbon atom of the benzene ring, a heterocycle optionally oxygen-containing or nitrogen-containing, which can be substituted with at least one $C_1$-$C_4$ alkyl radical; and a 4'-aminophenyl radical,
$R_3$ and $R'_3$, which may be identical or different, are chosen from a hydrogen atom and a halogen atom selected from chlorine, bromine, iodine and fluorine, a cyano, $C_1$-$C_4$ alkyl, $C_1$-$C_4$ alkoxy and acetyloxy radical,
$X^-$ represents an anion for example selected from chloride, methyl sulphate, and acetate,
A represents a group selected from the following structures A1 to A18, such as A1, A4, A7, A13 and A18:

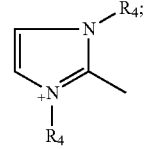
A1

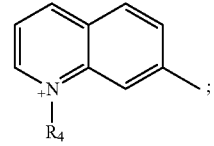
A2

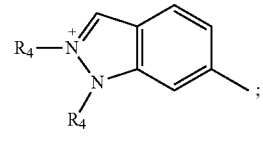
A3

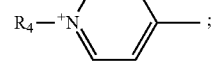
A4

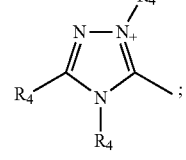
A5

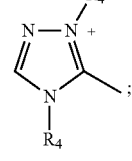
A6

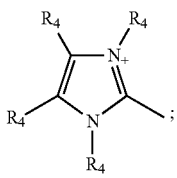
A7

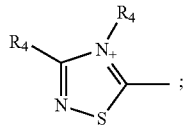
A8

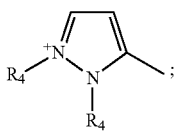

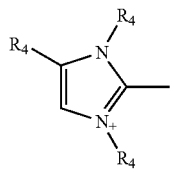
A9

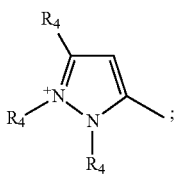

wherein $R_4$ represents a $C_1$-$C_4$ alkyl radical which can be substituted with a hydroxyl radical, and $R_5$ represents a $C_1$-$C_4$ alkoxy radical;

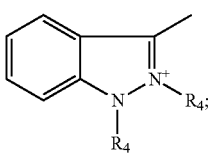
A10

$$B-N=N-\underset{R_9}{\overset{R_8}{\bigcirc}}-N\underset{R_7}{\overset{R_6}{\diagup}} \quad (II)$$
$$X^-$$

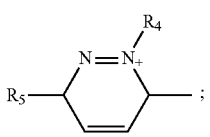
A11 wherein:

$R_6$ is chosen from a hydrogen atom and a $C_1$-$C_4$ alkyl radical, $R_7$ is chosen from a hydrogen atom, an alkyl radical which can be substituted with a —CN radical or with an amino group, and 4'-aminophenyl radical, or forms with $R_6$ a heterocycle optionally oxygen-containing or nitrogen-containing, which can be substituted with a $C_1$-$C_4$ alkyl radical,

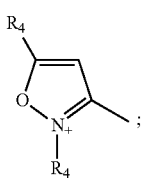
A12

$R_8$ and $R_9$, which may be identical or different, are chosen from a hydrogen atom, a halogen atom such as bromine, chlorine, iodine or fluorine, a $C_1$-$C_4$ alkyl or $C_1$-$C_4$ alkoxy radical, and a —CN radical,

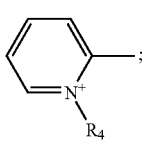
A13

$X^-$ represents an anion for example selected from chloride, methyl sulphate, and acetate, B represents a group selected from the following structures B1 to B6:

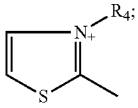
A14

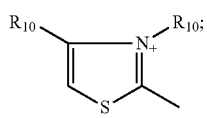
B1

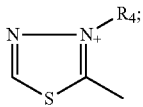
A15

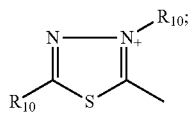
B2

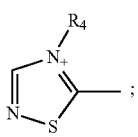
A16

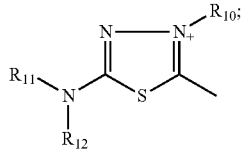
B3

-continued

B4

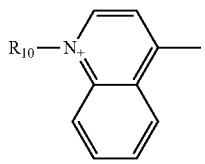
B5

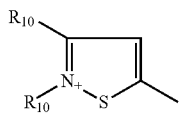
B6 wherein $R_{10}$ represents a $C_1$-$C_4$ alkyl radical, $R_{11}$ and $R_{12}$, which may be identical or different, are chosen from a hydrogen atom and a $C_1$-$C_4$ alkyl radical;

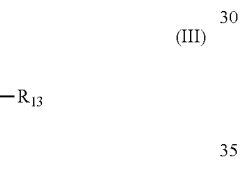
(III)

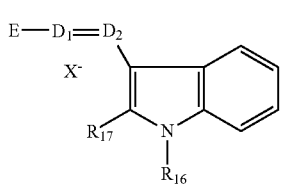
(III')

wherein:

$R_{13}$ is chosen from a hydrogen atom, a $C_1$-$C_4$ alkoxy radical, and a halogen atom such as bromine, chlorine, iodine, or fluorine, $R_{14}$ is chosen from a hydrogen atom and a $C_1$-$C_4$ alkyl radical, or forms, with a carbon atom of the benzene ring, a heterocycle optionally oxygenated and/or substituted with at least one $C_1$-$C_4$ alkyl group, $R_{15}$ is chosen from a hydrogen atom and a halogen atom such as bromine, chlorine, iodine, or fluorine, $R_{16}$ and $R_{17}$, which may be identical or different, are chosen from a hydrogen atom and a $C_1$-$C_4$ alkyl radical, $D_1$ and $D_2$, which may be identical or different, are chosen from a nitrogen atom and —CH group, m=0 or 1, such as 1, it being understood that when $R_{13}$ represents an unsubstituted amino group, $D_1$ and $D_2$ represent simultaneously a —CH group, and m=0, $X^-$ represents an anion for example selected from chloride, methyl sulphate, and acetate, E represents a group selected from the following structures E1 to E8, for example E1, E2, and E7:

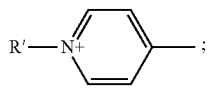
E1

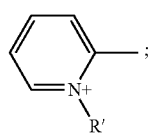
E2

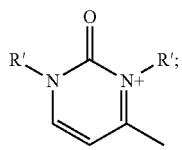
E3

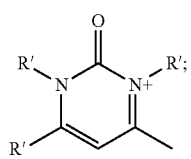
E4

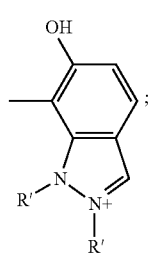
E5

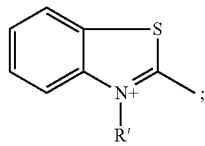
E6

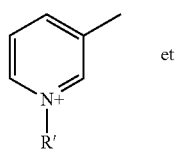
et
E7

-continued

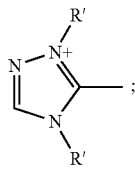

E8 wherein R' represents a $C_1$-$C_4$ alkyl radical; and when m=0 and $D_1$ represents a nitrogen atom, E can also denote a group of the following structure E9:

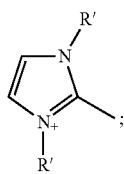

E9 wherein R' represents a $C_1$-$C_4$ alkyl radical.

(IV)

wherein:

the symbol G represents a group selected from the following structures $G_1$ to $G_3$:

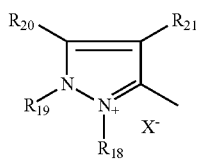

$G_1$

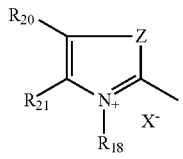

$G_2$

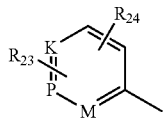

$G_3$ wherein $R_{18}$ is chosen from a $C_1$-$C_4$ alkyl radical, a phenyl radical which can be substituted with a $C_1$-$C_4$ alkyl radical, and a halogen atom selected from chlorine, bromine, iodine, and fluorine;

$R_{19}$ is chosen from a $C_1$-$C_4$ alkyl radical and a phenyl radical;

$R_{20}$ and $R_{21}$, which may be identical or different, are chosen from a $C_1$-$C_4$ alkyl radical and a phenyl radical, or form together in $G_1$ a benzene ring substituted with at least one $C_1$-$C_4$ alkyl, $C_1$-$C_4$ alkoxy, or $NO_2$ radical, or form together in $G_2$ a benzene ring optionally substituted with at least one $C_1$-$C_4$ alkyl, $C_1$-$C_4$ alkoxy, or $NO_2$ radical;

$R_{20}$ can in addition denote a hydrogen atom;

Z is chosen from an oxygen atom, a sulphur atom, and a group —$NR_{19}$;

M is chosen from a —CH, —CR group (R denoting $C_1$-$C_4$ alkyl), and —$NR_{22}(X^-)_r$;

K is chosen from a —CH, —CR group (R denoting $C_1$-$C_4$ alkyl), and —$NR_{22}(X^-)_r$;

P is chosen from a —CH, —CR group (R denoting $C_1$-$C_4$ alkyl), and —$NR_{22}(X^-)_r$; r is chosen from zero and 1;

$R_{22}$ is chosen from an atom $O^-$, a $C_1$-$C_4$ alkoxy radical, and a $C_1$-$C_4$ alkyl radical;

$R_{23}$ and $R_{24}$, which may be identical or different, are chosen from a hydrogen atom, a halogen atom selected from chlorine, bromine, iodine, and fluorine, a $C_1$-$C_4$ alkyl, a $C_1$-$C_4$ alkoxy radical, and an —$NO_2$ radical;

$X^-$ represents an anion for example selected from chloride, iodide, methyl sulphate, ethyl sulphate, acetate, and perchlorate;

provided that, if $R_{22}$ denotes $O^-$, then r denotes zero;

if K or P or M denote —N-alkyl $C_1$-$C_4X^-$, then $R_{23}$ or $R_{24}$ is for example different from a hydrogen atom;

if K denotes —$NR_{22}(X^-)_r$, then M=P=—CH, —CR;

if M denotes —$NR_{22}(X^-)_r$, then K=P=—CH, —CR;

if P denotes —$NR_{22}(X^-)_r$, then K=M and they denote —CH or —CR;

if Z denotes a sulphur atom with $R_{21}$ denoting $C_1$-$C_4$ alkyl, then $R_{20}$ is different from a hydrogen atom;

if Z denotes —$NR_{22}$ with $R_{19}$ denoting $C_1$-$C_4$ alkyl, then at least one of the radicals $R_{18}$, $R_{20}$ and $R_{21}$ of the group of structure $G_2$ is different from a $C_1$-$C_4$ alkyl radical;

the symbol J represents:

(a) a group with the following structure $J_1$:

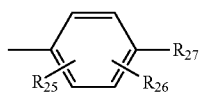

$J_1$ wherein:

$R_{25}$ is chosen from a hydrogen atom, a halogen atom selected from chlorine, bromine, iodine and fluorine, a $C_1$-$C_4$ alkyl radical, $C_1$-$C_4$ alkoxy radical, and a radical —OH, —$NO_2$, —$NHR_{28}$, —$NR_{29}R_{30}$, or —NHCOalkyl $C_1$-$C_4$, or forms with $R_{26}$ a ring with 5 or 6 ring members containing, or not containing, at least one heteroatom selected from nitrogen, oxygen, and sulphur;

$R_{26}$ is chosen from a hydrogen atom, a halogen atom selected from chlorine, bromine, iodine, and fluorine, a $C_1$-$C_4$ alkyl radical, and a $C_1$-$C_4$ alkoxy radical, or forms with $R_{27}$ or $R_{28}$ a ring with 5 or 6 ring members containing, or not containing, at least one heteroatom selected from nitrogen, oxygen, and sulphur;

$R_{27}$ is chosen from a hydrogen atom, a radical —OH, a radical —$NHR_{28}$, and a radical —$NR_{29}R_{30}$;

$R_{28}$ is chosen from a hydrogen atom, a $C_1$-$C_4$ alkyl radical, a $C_1$-$C_4$ monohydroxyalkyl radical, $C_2$-$C_4$ polyhydroxyalkyl radical, and a phenyl radical;

$R_{29}$ and $R_{30}$, which may be identical or different, are chosen from a $C_1$-$C_4$ alkyl radical, a $C_1$-$C_4$ monohydroxyalkyl radical, and $C_2$-$C_4$ polyhydroxyalkyl radical;

(b) a nitrogen-containing heterocyclic group with 5 or 6 ring members that can contain other heteroatoms and/or carbonylated groups and can be substituted with at least one $C_1$-$C_4$ alkyl, amino or phenyl radical, and for example a group with the following structure $J_2$:

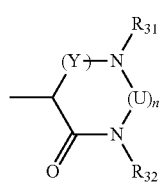

wherein:

$R_{31}$ and $R_{32}$, which may be identical or different, are chosen from a hydrogen atom, a $C_1$-$C_4$ alkyl radical, and a phenyl radical;

Y is chosen from the radical —CO— and the radical

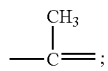

n=0 or 1, and, when n denotes 1, U denotes the radical —CO—.

In the structures of the dyes (I) to (IV) defined above, the $C_1$-$C_4$ alkyl or alkoxy group may for example denote methyl, ethyl, butyl, methoxy, or ethoxy.

Among the dyes of formulae (I) and (III), the following compounds may for example be used:

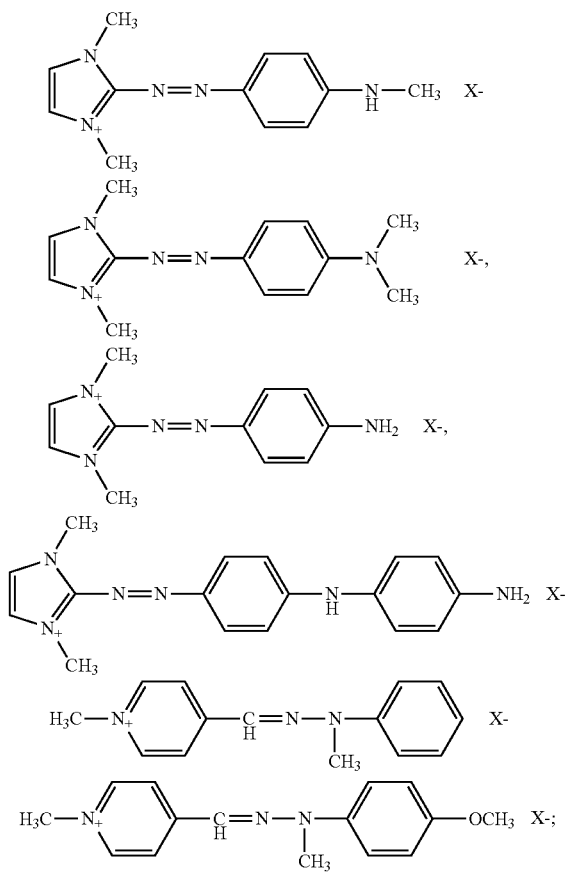

Non-limiting mention may also be made, among the azo direct dyes, of the following dyes, described in COLOR INDEX INTERNATIONAL 3rd edition:
Disperse Red 17
Basic Red 22
Basic Red 76
Basic Yellow 57
Basic Brown 16
Basic Brown 17
Disperse Black 9.

Non-limiting mention may also be made of 1-(4'-aminodiphenylazo)-2-methyl-4-bis(β-hydroxyethyl)aminobenzene.

Among the quinone direct dyes non-limiting mention may be made of the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
as well as the following compounds:
1-N-methylmorpholiniumpropylamino-4-hydroxy anthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)-anthraquinone.

Among the azine dyes, non-limiting mention may for example be made of the following compounds:
Basic Blue 17
Basic Red 2.

Among the triarylmethane dyes usable according to the present disclosure, non-limiting mention may for example be made of the following compounds:
Basic Green 1
Basic Violet 3
Basic Violet 14
Basic Blue 7
Basic Blue 26

Among the indoamine dyes usable according to the present disclosure, non-limiting mention may be made of the following compounds:
2-β-hydroxyethlyamino-5-[bis(β-4'-hydroxyethyl)amino] anilino-1,4-benzoquinone
2-β-hydroxyethylamino-5-(2'-methoxy-4'-amino)anilino-1,4-benzoquinone
3-N(2'-chloro-4'-hydroxy)phenyl-acetylamino-6-methoxy-1,4-benzoquinone imine
3-N(3'-chloro-4'-methylamino)phenyl-ureido-6-methyl-1,4-benzoquinone imine
3-[4'-N-(ethyl,carbamylmethyl)-amino]-phenyl-ureido-6-methyl-1,4-benzoquinone imine.

Among the dyes of the tetraazapentamethine type usable according to the present disclosure, non-limiting mention may for example be made of the compounds shown in the following table:

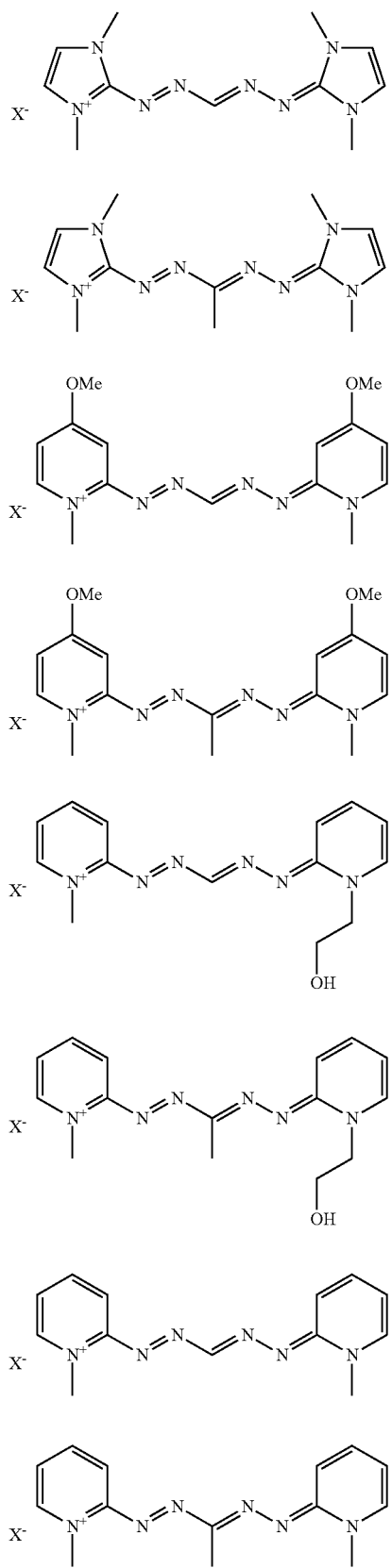

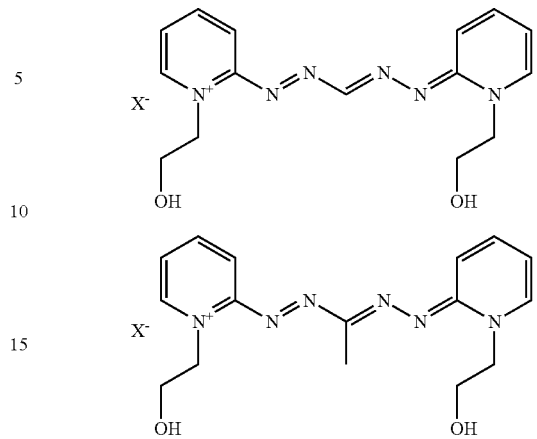

X⁻ represents an anion for example selected from chloride, iodide, methyl sulphate, ethyl sulphate, acetate, and perchlorate.

Among the polychromophoric dyes, non-limiting mention may for example be made of the di- or tri-chromophoric azo and/or azomethine (hydrazone) dyes, symmetrical or not, comprising for instance at least one aromatic heterocycle comprising 5 or 6 ring members, optionally condensed, comprising at least one quaternized nitrogen atom inserted in said heterocycle and optionally at least one other heteroatom (such as nitrogen, sulphur, oxygen), and in addition, at least one phenyl or naphthyl group, optionally substituted, optionally bearing at least one group OR with R being chosen from a hydrogen atom, an optionally substituted $C_1$-$C_6$ alkyl radical, and a phenyl nucleus optionally substituted, or at least one group N(R')$_2$ with R' identical or not, being chosen from a hydrogen atom, an optionally substituted $C_1$-$C_6$ alkyl radical, and a phenyl nucleus optionally substituted; and the radicals R' can form, with the nitrogen atom to which they are bound, a saturated heterocycle with 5 or 6 ring members, or alternatively the one and/or the two radicals R' can each form, with the carbon atom of the aromatic ring positioned ortho to the nitrogen atom, a saturated heterocycle with 5 or 6 ring members.

As aromatic cationic heterocycle, non-limiting mention may for example be made of rings with 5 or 6 ring members comprising 1 to 3 nitrogen atoms, such as 1 or 2 nitrogen atoms, one being quaternized; said heterocycle being moreover optionally condensed to a benzene ring. It should also be noted that the heterocycle can optionally comprise another heteroatom different from nitrogen, such as sulphur or oxygen.

If the heterocycles or phenyl or naphthyl groups are substituted, they may for example be substituted with at least one of the radical: $C_1$-$C_8$ alkyl optionally substituted with a hydroxyl group, $C_1$-$C_2$ alkoxy, $C_2$-$C_4$ hydroxyalkoxy, acetylamino, amino substituted with one or two $C_1$-$C_4$ alkyl radicals, optionally bearing at least one hydroxyl group or the two radicals can form, with the nitrogen atom to which they are attached, a heterocycle with 5 or 6 ring members, optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; an amino radical substituted with one or two $C_1$-$C_4$ alkyl radicals, which may be identical or different, optionally bearing at least one hydroxyl group.

These polychromophores may be joined together by means of at least one linkage optionally comprising at least one quaternized nitrogen atom inserted or not in a heterocycle, saturated or not, optionally aromatic.

In at least one embodiment, the linkage is a linear, branched or cyclic $C_1$-$C_{20}$ alkyl chain, optionally interrupted by at least one heteroatom (such as nitrogen, oxygen) and/or by at least one group comprising one (CO, $SO_2$), optionally interrupted by at least one heterocycle, condensed or not with a phenyl nucleus and comprising at least one quaternized nitrogen atom inserted in said ring and optionally at least one other heteroatom (such as oxygen, nitrogen or sulphur), optionally interrupted by at least one phenyl or naphthyl group, substituted or unsubstituted, optionally at least one quaternary ammonium group substituted with two $C_1$-$C_{15}$ alkyl groups optionally substituted; the linkage not comprising a nitro, nitroso or peroxo group.

The bond between the linkage and each chromophore may generally be provided by a heteroatom substituting the phenyl or naphthyl nucleus or by the quaternized nitrogen atom of the cationic heterocycle.

The dye can comprise chromophores that are identical or different.

For examples of such dyes, non-limiting mention may be made of those disclosed in patent applications EP 1637566, EP 1619221, EP 1634926, EP 1619220, EP 1672033, EP 1671954, EP 1671955, EP 1679312, EP 1671951, EP 167952, EP 167971, WO 06/063866, WO 06/063867, WO 06/063868, WO 06/063869, EP 1408919, EP 1377264, EP 1377262, EP 1377261, EP 1377263, EP 1399425, EP 1399117, EP 1416909, EP 1399116, and EP 1671560.

It is also possible to use cationic direct dyes mentioned for example in applications EP 1006153, which for instance describes dyes comprising two chromophores of the anthraquinone type connected by a cationic linkage; EP 1433472, EP 1433474, EP 1433471 and EP 1433473 which for instance describe dichromophoric dyes, identical or not, connected by a cationic or non-cationic linkage, as well as EP 6291333 which for example describes dyes comprising three chromophores, one of them being an anthraquinone chromophore, to which two chromophores of the azo or diazacarbocyanine type or one of its isomers may be joined.

Among the natural direct dyes usable according to the present disclosure, non-limiting mention may for example be made of lawsone, juglone, alizarin, purpurine, carminic acid, kermesic acid, purpurogallin, protocatechaldehyde, indigo, isatin, curcumin, spinulosin, apigenidin, and orceins. It is also possible to use extracts or decoctions containing these natural dyes, such as cataplasms or extracts based on henna.

When present, the at least one direct dye may for example be present in a total amount ranging from 0.0001 to 10 wt. % of the total weight of composition (A), such as from 0.005 to 5 wt. %.

According to at least one embodiment of the agent disclosed herein, neither composition (A) nor composition (B) comprises at least one direct dye and/or at least one oxidation dye (bases and couplers). Or, if at least one of compositions (A) and (B) comprises at least one direct dye and/or at least one oxidation dye, the at least one direct dye and/or at least one oxidation dye are present in a total amount of less than 0.005 wt. % relative to the total weight of the respective composition(s).

In this embodiment, the agent according to the present disclosure may for example be used for bleaching keratin fibers.

In at least one embodiment, composition (A) can for example comprise at least one solid or pasty, and for example pulverulent, additive. The at least one additive can be selected from clays, salts different from ammonium salts, anionic, non-ionic, cationic, or zwitterionic surfactants, natural or synthetic thickeners, starch optionally modified, glass beads, silica, nylon, alumina, titanium dioxide, zeolites, poly(methyl methacrylate) (PMMA), chitosan, maltodextrin, cyclodextrin, mono- or disaccharides such as glucose, sucrose, sorbitol or fructose, zinc oxide, zirconium oxide, silicabades, talc, borosilicates for example of calcium, polyethylene, polytetrafluoroethylene (PTFE), cellulose and its derivatives, superabsorbent compounds, carbonates of magnesium or of calcium, polyacrylamide, porous hydroxyapatite, sawdust, powdered fucus, crosslinked polyvinylpyrrolidone, calcium alginate, activated charcoal, particles of poly(vinylidene chloride/acrylonitrile), for example those marketed under the general name EXPANCEL® by the company AKZO NOBEL such as under the references EXPANCEL® WE or DE EXPANCELS, and mixtures thereof.

Generally, compositions (A) and (B) may be formulated in a cosmetically acceptable medium, which generally comprises water and/or at least one organic solvent.

As the at least one organic solvent, non-limiting mention may for example be made of the linear or branched $C_2$-$C_4$ alkanols, such as ethanol and isopropanol; glycerol; the polyols and polyol ethers such as 2-butoxyethanol, propylene glycol, dipropylene glycol, monomethyl ether of propylene glycol, monoethyl ether and monomethyl ether of diethylene glycol, as well as aromatic alcohols such as benzyl alcohol or phenoxyethanol, and mixtures thereof.

The at least one organic solvent can be present in a total amount ranging from 1 to 40 wt. % relative to the total weight of each composition in which it is contained, such as from 5 to 30 wt. %.

In at least one embodiment, compositions (A) and (B) comprise water. For example, each of compositions (A) and (B) may comprise at least 5 wt. % of water, for example at least 10 wt. % of water, such as at least 20 wt. % of water, relative to its total weight.

Compositions (A) and/or (B) according to the present disclosure can also comprise at least one additive, selected from those typically used in compositions for coloring and/or bleaching keratin fibers such as polymeric conditioners, for instance cationic; thickeners; antioxidants different from the at least one reductone; penetrating agents; sequestering agents; perfumes; dispersants; film-forming agents; ceramides; preservatives; and opacifiers.

The at least one additive can generally each be present in an amount ranging from 0.01 to 20 wt. %, relative to the weight of each composition.

According to at least one embodiment, composition (A) is in the form of an oil-in-water emulsion (called "direct emulsion"), or of a water-in-oil emulsion (called "inverse emulsion").

The present disclosure also relates to a method of coloring and/or bleaching keratin fibers, comprising applying an agent as described herein on said the keratin fibers.

According to the present disclosure, the agent applied on the keratin fibers results from mixing compositions (A) and (B) either before application on the keratin fibers (extemporaneous preparation), or directly on the keratin fibers (successive application of compositions (A) and (B) on the fibers without intermediate rinsing).

Thus, according to at least one embodiment of the method disclosed herein, a method of coloring and/or bleaching keratin fibers comprises:

applying, to wet or dry keratin fibers, composition (A) comprising at least one alkalizing agent, and successively applying, to the wet or dry keratin fibers, composition (B) comprising at least one oxidizing agent, without intermediate rinsing, wherein at least one of the compositions (A) and (B) comprises at least one fat selected from liquid hydrocarbons, such that the at least one fat is present in a mixture of compositions (A) and (B) in an amount of at least 20 wt. %, relative to the total weight of the mixture, and further wherein at least one of compositions (A) and (B) comprises at least one reductone.

In another embodiment of the method disclosed herein, a method of coloring and/or bleaching keratin fibers comprises the application of the agent by extemporaneously mixing composition (A) comprising at least one alkalizing agent and composition (B) comprising at least one oxidizing agent, and applying the resulting mixture to wet or dry keratin fibers, wherein at least one of the compositions (A) and (B) comprises at least one fat selected from liquid hydrocarbons, such that the at least one fat is present in a mixture of compositions (A) and (B) in an amount of at least 20 wt. %, relative to the total weight of the mixture, and further wherein at least one of the compositions (A) and (B) comprises at least one reductone.

In this embodiment, the time between mixing compositions (A) and (B) and applying the resulting mixture on the keratin fibers for example does not exceed 30 minutes, and for instance does not exceed 10 minutes, such as 5 minutes.

Regardless of the method employed, composition (A) and composition (B) may be mixed together at a weight ratio value ranging from 0.2 to 3, such as from 0.3 to 1.

Moreover, independently of the method employed, the mixture (resulting either from extemporaneous mixing of compositions (A) and (B) or from successively applying the compositions) may be left on the fibers for a period of time ranging from 1 minute to 1 hour, such as from 5 minutes to 30 minutes.

The temperature during the treatment may conventionally range from room temperature (ranging from 15 to 25° C.) to 80° C., for example from room temperature to 60° C.

At the end of the treatment, the keratin fibers may optionally be rinsed with water, and optionally washed with a shampoo followed by rinsing with water, before being dried or left to dry.

Finally, the present disclosure also relates to a multi-compartment device or "kit" for coloring and/or bleaching keratin fibers, consisting of:

a first compartment containing composition (A) comprising at least one alkalizing agent, and a second compartment containing composition (B) comprising at least one oxidizing agent, wherein at least one of the compositions (A) and (B) comprises at least one fat selected from liquid hydrocarbons, such that the at least one fat is present in a mixture of compositions (A) and (B) in an amount of at least 20 wt. %, relative to the total weight of the mixture, and further wherein at least one of the compositions (A) and (B) comprises at least one reductone.

The multi-compartment device can for example be equipped with devices for delivering the desired mixture onto the hair, such as the devices described in patent FR 2586913.

The multi-compartment device can be accompanied by at least one composition for washing and/or conditioning keratin fibers, for application before and/or after the coloring and/or bleaching treatment according to the present disclosure.

The following example serves to illustrate the disclosure but is not limiting.

EXAMPLE

Agents for oxidation dyeing were prepared. Compositions "A1" and "A2" for oxidation dyeing were prepared according to the following table, where the amounts are expressed in grams:

Dyeing Composition (A):

| Composition | A1 | A2 |
|---|---|---|
| Liquid paraffin | 55 | 55 |
| Octyl dodecanol | 10 | 10 |
| Hectorite modified distearyl dimethyl ammonium | 1.5 | 1.5 |
| Propylene carbonate | 0.5 | 0.5 |
| Oleic alcohol 10 EO | 5 | 5 |
| Propylene glycol | 2 | 2 |
| Ethanol | 2.5 | 2.5 |
| Hexylene glycol | 1 | 1 |
| Dipropylene glycol | 1 | 1 |
| Monoethanolamine | 4.5 | 4.5 |
| POE/POP/POE (Poloxamer 184) | 9 | 9 |
| Ascorbic acid | — | 0.25 |
| Para-phenylenediamine | 0.16 | 0.16 |
| Para-aminophenol | 0.12 | 0.12 |
| 5-amino-6-chloro-o-cresol | 0.2 | 0.2 |
| 1-H-pyrazole-1-ethanol-4,5-diaminosulphate | 1.44 | 1.44 |
| 1-methyl-2-hydroxy-4-aminobenzene | 0.92 | 0.92 |
| Water | Q.s. 100 | Q.s. 100 |

Composition A2 corresponds to a composition (A) according to the present disclosure, whereas composition A1 is a comparative composition not containing at least one reductone.

Oxidizing Composition (B):

| Composition | B |
|---|---|
| Aqueous solution with 40 wt. % of diethylene triamine pentaacetic acid, pentasodium salt | 0.375 |
| Aqueous solution with 50 wt. % of hydrogen peroxide | 12 |
| Sodium stannate | 0.04 |
| Tetrasodium pyrophosphate | 0.03 |
| Liquid paraffin | 20 |
| Aqueous solution with 40 wt. % of tetramethyl hexamethylenediamine/dichloro-1,3-propylene polycondensate or Hexadimethrine chloride | 0.1 |
| Aqueous solution with 40 wt. % of polydimethyl diallyl ammonium chloride or Polyquaternium-6, unstabilized | 0.2 |
| Glycerine | 0.5 |
| Cetearyl alcohol | 8 |
| Ethoxylated cetylstearyl alcohol (33 EO) | 3 |
| Ethoxylated amide of colza acids (4 EO) | 1.2 |
| Vitamin E: DL-α-tocopherol | 0.1 |
| Phosphoric acid | Qs pH 2.2 |
| Water | Q.s. 100 |

The compositions described above were mixed at the moment of use, as follows:

10 g of dyeing composition A1 was mixed with 10 g of oxidizing composition B;

10 g of dyeing composition A2 was mixed with 10 g of oxidizing composition B.

The agent "C2," the resulting mixture of compositions A2 and B, was less colored than the agent "C1," the resulting mixture of compositions A1 and B.

The agents were each separately applied to hair. Agent C2 led to more homogeneous and intense hair color, relative to hair treated with agent C1.

What is claimed is:

1. An agent for coloring and/or bleaching keratin fibers, consisting of:
    a first composition (A) comprising at least one alkalizing agent, and
    a second composition (B) comprising at least one oxidizing agent,
    wherein at least one of the two compositions (A) and (B) comprises at least one fat selected from liquid hydrocarbons, such that the at least one fat is present in a mixture of compositions (A) and (B) in an amount of at least 20 wt. %, relative to the total weight of the mixture, and
    further wherein at least one of compositions (A) and (B) comprises at least one reductone optionally in a form chosen from acids, salts, and esters.

2. The agent according to claim 1, wherein the at least one alkalizing agent is selected from ammonia, alkaline carbonates, sodium hydroxide, potassium hydroxide, organic amines, and compounds of formula (I):

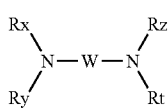

(I)

wherein W is chosen from $C_1$-$C_6$ alkylene residues optionally substituted with a hydroxyl group and $C_1$-$C_6$ alkyl radicals; and Rx, Ry, Rz, and Rt, which may be identical or different, are chosen from a hydrogen atom, $C_1$-$C_6$ alkyls, $C_1$-$C_6$ hydroxyalkyls, and $C_1$-$C_6$ aminoalkyl radicals.

3. The agent according to claim 2, wherein the at least one alkalizing agent is selected from organic amines chosen from alkanolamines and the derivatives thereof.

4. The agent according to claim 1, wherein the at least one oxidizing agent is selected from hydrogen peroxide, urea peroxide, bromates or ferricyanides of alkali metals, peroxidized salts, and redox enzymes.

5. The agent according to claim 4, wherein the at least one oxidizing agent is selected from peroxidized salts chosen from persulphates, perborates, and percarbonates of alkali metals or alkaline-earth metals.

6. The agent according to claim 4, wherein the at least one oxidizing agent is selected from redox enzymes chosen from laccases, peroxidises, and 2-electron oxidoreductases, optionally in the presence of the respective donor or cofactor thereof.

7. The agent according to claim 4, wherein the at least one oxidizing agent is hydrogen peroxide.

8. The agent according to claim 1, wherein the at least one reductone is chosen from compounds of formula (II):

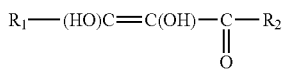

(II)

wherein $R_1$ and $R_2$, which may be identical or different, each denote a group containing at least one carbon atom and/or oxygen atom, and $R_1$ and $R_2$ can form, with the three carbon atoms of the compounds of formula (II), a ring whose additional constituent atoms are constituted of carbon atoms and/or oxygen atoms.

9. The agent according to claim 8, wherein $R_1$ and $R_2$ form, with the three carbon atoms of the compounds of formula (II), a ring with 5 or 6 ring members, whose additional constituent atoms are constituted of carbon atoms and/or oxygen atoms.

10. The agent according to claim 8, wherein the at least one reductone is in a form chosen from salts of alkali metals and salts of alkaline-earth metals.

11. The agent according to claim 8, wherein the at least one reductone is in the form of an ester of $C_8$ to $C_{30}$ fatty acids.

12. The agent according to claim 1, wherein the at least one reductone is selected from ascorbic acid, erythorbic acid, and salts thereof.

13. The agent according to claim 12, wherein the at least one reductone is selected from the sodium and potassium salts thereof.

14. The agent according to claim 1, wherein the at least one reductone, when present in acid form in composition (A), is present in an amount ranging from 0.01 to 1 wt. %, relative to the total weight of composition (A).

15. The agent according to claim 14, wherein the at least one reductone is present in an amount ranging from 0.1 to 0.25 wt. %, relative to the total weight of composition (A).

16. The agent according to claim 1, wherein the at least one reductone, when present in acid form in composition (B), is present in an amount ranging from 0.01 to 1 wt. %, relative to the weight of composition (B).

17. The agent according to claim 16, wherein the at least one reductone is present in an amount ranging from 0.1 to 0.25 wt. %, relative to the total weight of composition (B).

18. The agent according to claim 1, wherein the at least one reductone, in acid form, is present in the mixture of compositions (A) and (B) in a total amount ranging from 0.01 to 1 wt. %, relative to the total weight of the mixture.

19. The agent according to claim 18, wherein the at least one reductone is present in a total amount ranging from 0.1 to 0.2 wt. %, relative to the total weight of the mixture.

20. The agent according to claim 1, wherein the at least one liquid hydrocarbon is selected from:
    linear or branched, optionally cyclic, $C_6$-$C_{16}$ lower alkanes, and
    linear or branched hydrocarbons, of mineral, animal or synthetic origin, containing more than 16 carbon atoms.

21. The agent according to claim 20, wherein the at least one liquid hydrocarbon is selected from paraffin oils and liquid paraffin.

22. The agent according to claim 1, wherein the at least one liquid hydrocarbon is present in the mixture of compositions (A) and (B) in an amount of at least 25 wt. %, relative to the total weight of the mixture.

23. The agent according to claim 22, wherein the at least one liquid hydrocarbon is present in the mixture of compositions (A) and (B) in an amount of at least 30 wt. %, relative to the total weight of the mixture.

24. The agent according to claim 1, wherein composition (A) is in the form of an oil-in-water emulsion, or a water-in-oil emulsion.

25. The agent according to claim 1, wherein composition (A) further comprises at least one oxidation dye selected from oxidation bases and optionally combined with at least one coupler, and/or at least one direct dye.

26. The agent according to claim 1, wherein neither composition (A) nor composition (B) comprises at least one direct dye or at least one oxidation dye.

27. The agent according to claim 1, wherein if at least one of composition (A) and composition (B) comprises at least one direct dye and/or at least one oxidation dye, the at least one direct dye and/or at least one oxidation dye are present in a total amount of less than 0.005 wt. %, relative to the total weight of the respective composition.

28. A method of coloring and/or bleaching keratin fibers, comprising:
applying, to wet or dry keratin fibers, composition (A) comprising at least one alkalizing agent, and
successively applying, to the wet or dry keratin fibers, composition (B) comprising at least one oxidizing agent,
without intermediate rinsing,
wherein at least one of the compositions (A) and (B) comprises at least one fat selected from liquid hydrocarbons, such that the at least one fat is present in a mixture of compositions (A) and (B) in an amount of at least 20 wt. %, relative to the total weight of the mixture, and
further wherein at least one of compositions (A) and (B) comprises at least one reductone optionally in a form chosen from acids, salts, and esters.

29. A method of coloring and/or bleaching keratin fibers, comprising
extemporaneously mixing composition (A) comprising at least one alkalizing agent and composition (B) comprising at least one oxidizing agent, and
applying the resulting agent to wet or dry keratin fibers,
wherein at least one of the compositions (A) and (B) comprises at least one fat selected from liquid hydrocarbons, such that the at least one fat is present in a mixture of compositions (A) and (B) in an amount of at least 20 wt. %, relative to the total weight of the mixture, and
further wherein at least one of the compositions (A) and (B) comprises at least one reductone optionally in a form chosen from acids, salts, and esters.

30. A multi-compartment kit for coloring and/or bleaching keratin fibers, consisting of:
a first compartment containing composition (A) comprising at least one alkalizing agent, and
a second compartment containing composition (B) comprising at least one oxidizing agent,
wherein at least one of the compositions (A) and (B) comprises at least one fat selected from liquid hydrocarbons, such that the at least one fat is present in a mixture of compositions (A) and (B) in an amount of at least 20 wt. %, relative to the total weight of the mixture, and
further wherein at least one of the compositions (A) and (B) comprises at least one reductone optionally in a form chosen from acids, salts, and esters.

* * * * *